(12) United States Patent
Koster et al.

(10) Patent No.: US 11,992,586 B2
(45) Date of Patent: May 28, 2024

(54) BREAST SHIELD ARRANGEMENT FOR A BREAST PUMP

(71) Applicant: KONINKLIJKE PHILIPS N.V., Eindhoven (NL)

(72) Inventors: Aafje Gijsbertha Koster, Eindhoven (NL); Gertrude Riëtte Bakker-Van Der Kamp, Den Helder (NL); Daan Hendrik Gosenshuis, Waarle (NL); Johannes Tseard Van Der Kooi, Munein (NL); Lili-Marjan Brockhuis, Geldrop (NL); Christoph Dobrusskin, Nuenen (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 877 days.

(21) Appl. No.: 16/978,801

(22) PCT Filed: Mar. 4, 2019

(86) PCT No.: PCT/EP2019/055234
§ 371 (c)(1),
(2) Date: Sep. 8, 2020

(87) PCT Pub. No.: WO2019/174942
PCT Pub. Date: Sep. 19, 2019

(65) Prior Publication Data
US 2020/0405925 A1    Dec. 31, 2020

(30) Foreign Application Priority Data
Mar. 12, 2018  (EP) ..................................... 18161312

(51) Int. Cl.
*A61M 1/06* (2006.01)
*A61J 13/00* (2006.01)

(52) U.S. Cl.
CPC .............. *A61M 1/066* (2014.02); *A61J 13/00* (2013.01)

(58) Field of Classification Search
CPC ................................ A61M 1/066; A61J 13/00
See application file for complete search history.

(56) References Cited

U.S. PATENT DOCUMENTS

| 5,941,847 A | 8/1999 | Huber |
| 6,383,163 B1 | 5/2002 | Kelly |
| (Continued) | | |

FOREIGN PATENT DOCUMENTS

| FR | 1067421 | 6/1954 |
| JP | 2007089904 | 4/2007 |
| (Continued) | | |

OTHER PUBLICATIONS

Translation of JP 2007089904A (Year: 2007).*
(Continued)

*Primary Examiner* — Dung T Ulsh

(57) ABSTRACT

A breast shield arrangement (300) for a breast pump comprises a first sealing portion (310), a port (320) and an intermediate portion (330) coupled between the first sealing portion (310) and the port (320). The intermediate portion (330) comprises a circumferentially extending wall defining a first volume (V1) which is adapted to receive a part of a breast, a first end (331), a curved portion (332) and a second end (333). The curved portion (332) comprises a second sealing portion (332c) which is adapted to at least partially seal the curved portion (332) against the nipple (310), the areola (320) or the breast (200) when a vacuum is applied at the port (320) creating a second volume (V2) between the first sealing portion (310, 332c) of the breast (200). The curved portion (332) at the second volume is curved outwardly as seen from the first sealing portion (310).

20 Claims, 23 Drawing Sheets

(56) References Cited

U.S. PATENT DOCUMENTS

| | | | |
|---|---|---|---|
| 6,461,324 B1 | 10/2002 | Schlensog | |
| 8,052,635 B1 | 11/2011 | Kelly | |
| 8,323,235 B2 | 12/2012 | Bryan | |
| 9,248,223 B2 | 2/2016 | Van Der Kamp | |
| 9,603,982 B2 | 3/2017 | Silver | |
| 2012/0004604 A1 | 1/2012 | Van Der Kamp | |
| 2015/0065994 A1* | 3/2015 | Fridman | A61M 1/0697 604/74 |

FOREIGN PATENT DOCUMENTS

| | | |
|---|---|---|
| WO | 00/33987 | 6/2000 |
| WO | 2011/007140 | 1/2011 |
| WO | 2016033107 | 3/2016 |
| WO | 2018/041365 | 3/2018 |

OTHER PUBLICATIONS

International Search Report and Written Opinion dated May 23, 2019 for International Application No. PCT/EP2019/055234 Filed Mar. 4, 2019.

* cited by examiner

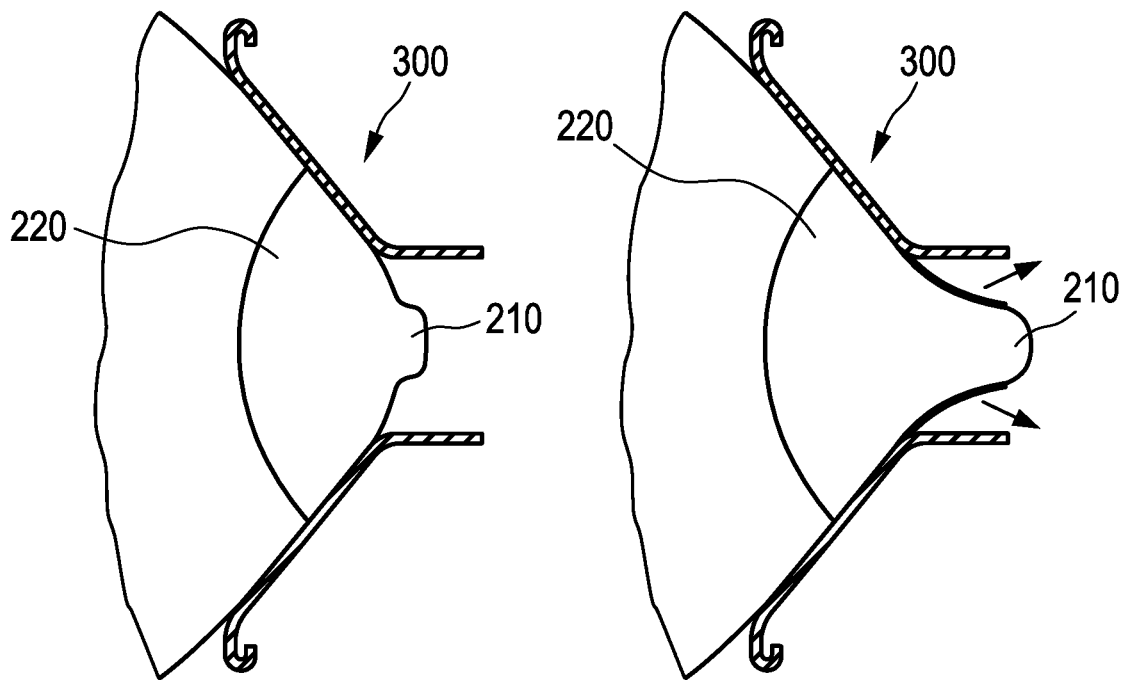
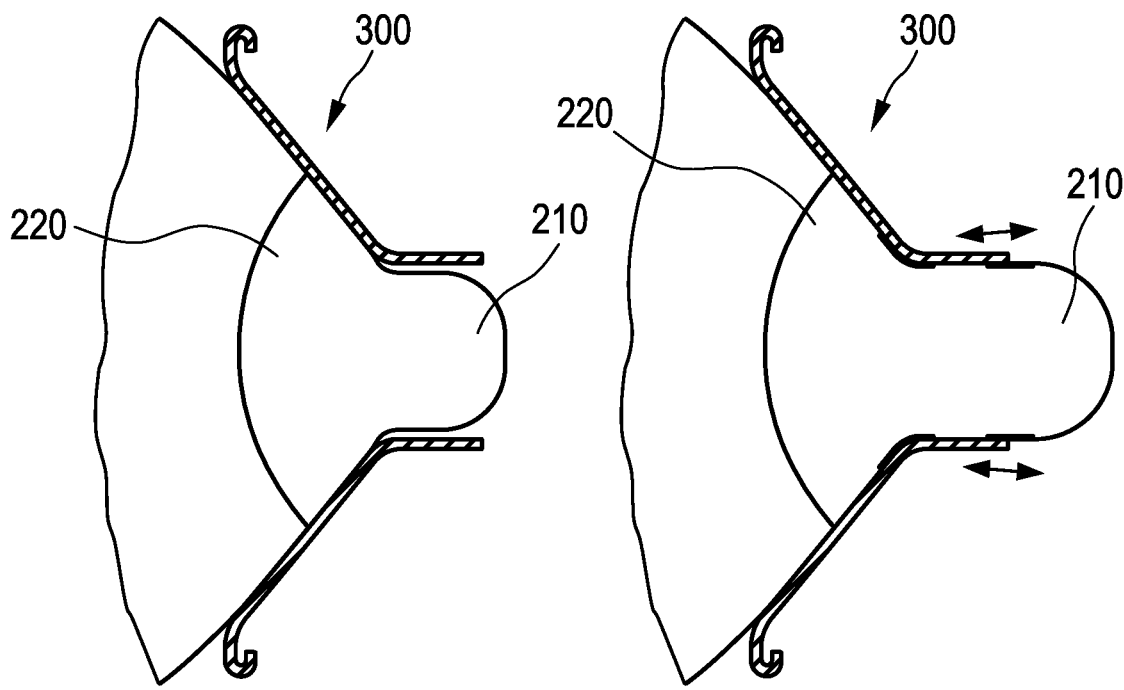
FIG. 8

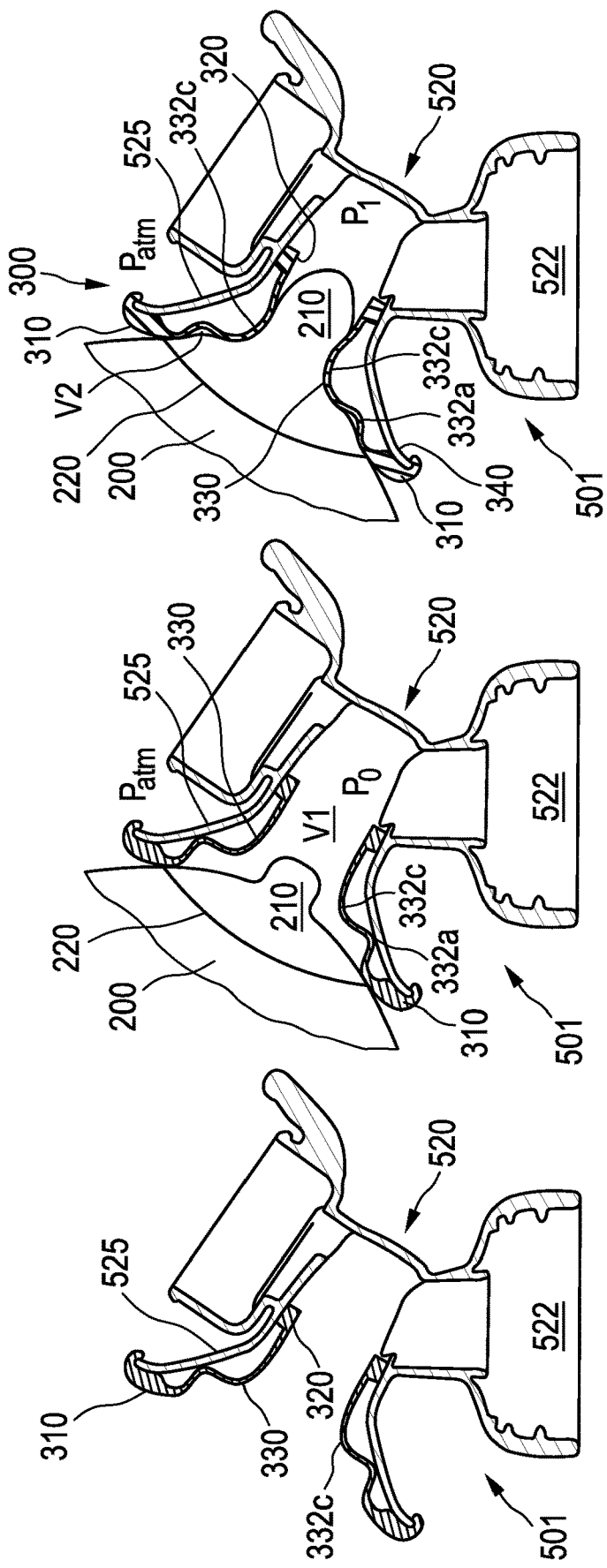

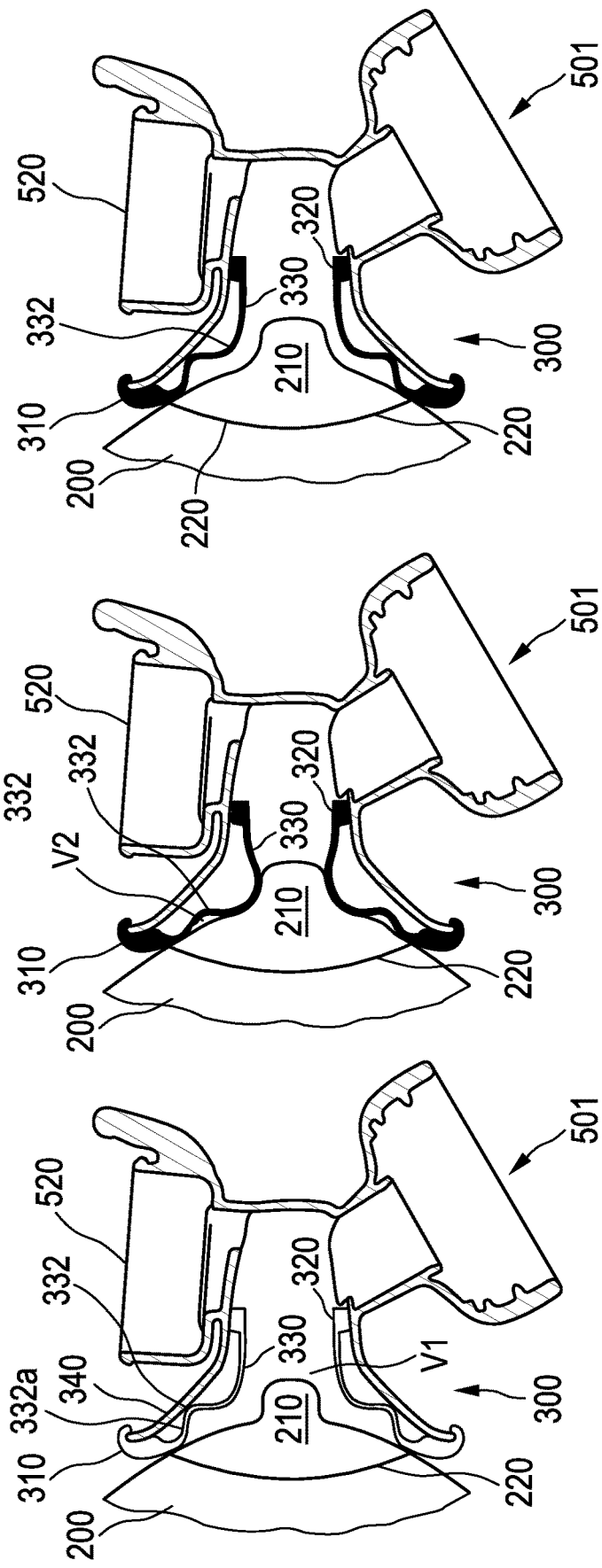

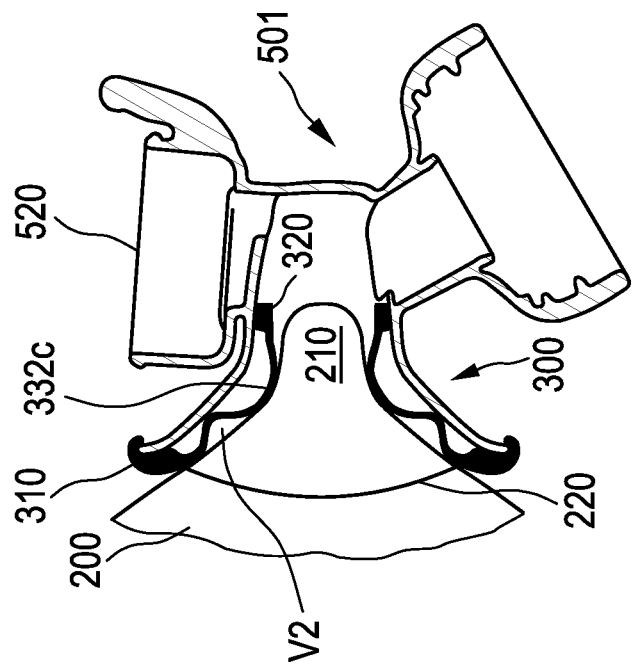
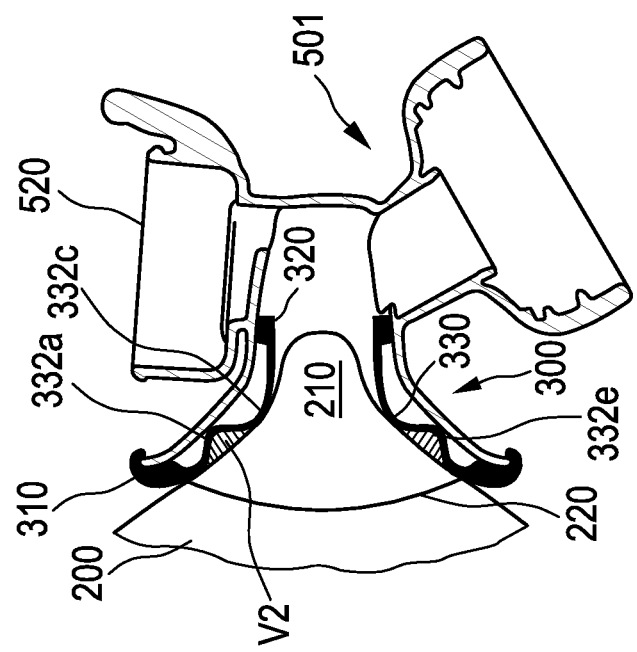
FIG. 18D
FIG. 18E

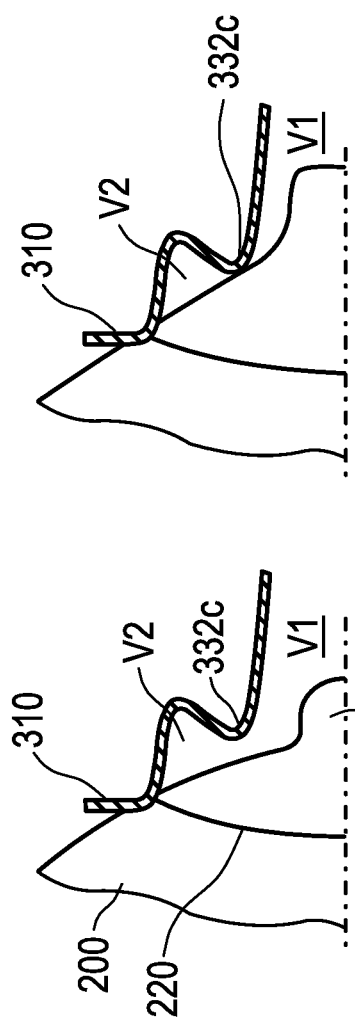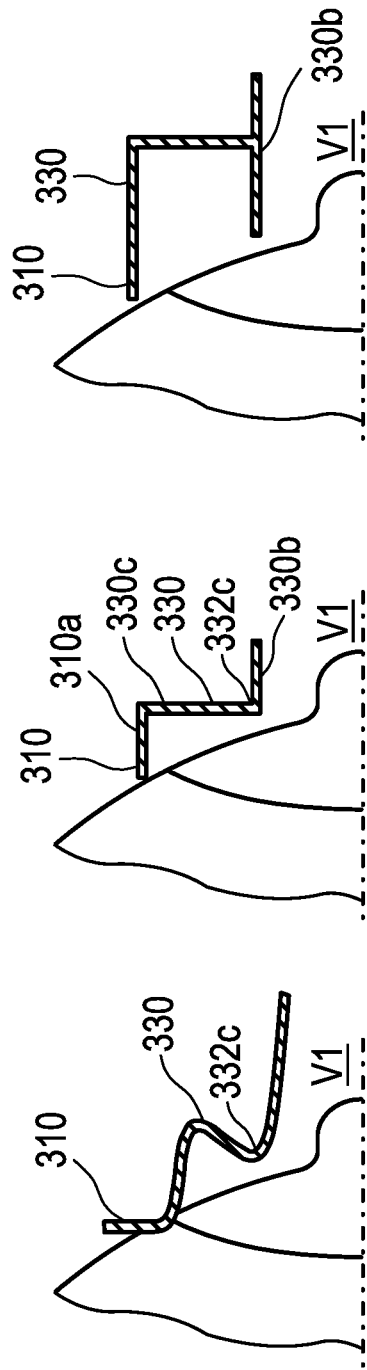
FIG. 19
FIG. 20

BREAST SHIELD ARRANGEMENT FOR A BREAST PUMP

CROSS REFERENCE TO RELATED APPLICATIONS

This application is the U.S. National Phase application under 35 U.S.C. § 371 of International Application No. PCT/EP2019/055234 filed Mar. 4, 2019, which claims the benefit of European Patent Application Number 18161312.6 filed Mar. 12, 2018. These applications are hereby incorporated by reference herein.

FIELD OF THE INVENTION

The invention relates to a breast shield arrangement for a breast pump as well as a breast pump and a method of operating a breast shield arrangement.

BACKGROUND OF THE INVENTION

Breast feeding is the natural way for feeding a baby. The WHO recommends exclusively breast feeding an infant for six months and then continuing breast feeding for at least up to the age of two years. If a mother is, however, not able to feed her infant directly, e.g. because of medical problems or because of absence, the use of a breast pump allows to extract milk and to feed the breast milk to the infant through other means like a bottle.

During breast feeding, an infant or baby performs a peristaltic tongue movement. At the same time, the infant will suck on the breast of the mother. By sucking on the breast of the mother, a negative pressure is created enabling the baby to form a teat from the breast nipple, the areola and the underlying breast tissue. The baby is able to hold a base vacuum in maintaining the teat in the mouth of the baby. In addition to the base vacuum, an alternating pressure is applied with the jaw and the tongue.

FIGS. 1A and 1B show schematically and exemplary a general anatomy of the sucking of an infant. In the FIGS. 1A and 1B, an infant or baby 100 with a tongue 110 having an anterior portion 111 and a posterior portion 112 is depicted. Furthermore, a breast 200 of the breast feeding woman including milk ducts 210, an areola 220 and a nipple 230 are depicted. The infant or baby 100 is able to maintain a base vacuum in the mouth such that the nipple 230 stays in the mouth. Furthermore, the baby 100 performs peristaltic tongue movements in order to extract milk from the breast of the breast feeding woman. The baby is also able to generate a wave with its tongue. As can be seen in FIG. 1A, the tongue 110 creates a hill or bump 113 (at its anterior portion) as well as a further hill or bump 114 (at its posterior portion 112). In between these two bumps 113, 114, a valley 116 is present. As can be seen in FIG. 1B, the bump or hill 113, 114 move along the tongue of the infant. The same applies to the valley 116, 117. The milk from the milk ducts 110 are thus transported in the valleys 116, 117 through the nipples 230 into the mouth of the infant. The presence of the hills 113, 114 enables the pushing of the milk towards the mouth of the infant. At the tip of the nipple, the presence of a valley 116, 117 increases in volume which is responsible for the vacuum creation at the tip of the nipple. At the same moment, the hills 113, 114 are pushing the milk towards the exit such that the infant 110 can drink the exited milk M. The movement of the tongue creating the hills and valleys is important to stimulate a hormone production responsible for the milk ejection reflex and keeping the milk flowing.

U.S. Pat. No. 9,248,223 B2 discloses an insert for a breast pump which collapses if a vacuum is applied by the breast pump.

JP 2007-089904 discloses a breast shield arrangement having a deformable funnel which is in contact with a breast when no vacuum is applied and which is not in contact if a vacuum is applied.

FR 1 067 421 discloses a breast shield arrangement with two ports through which separate vacuums can be applied. The breast shield arrangement comprises a funnel into which the breast of a user is placed. A first vacuum is applied via an open end of the funnel and a second vacuum is applied at the outside of the funnel.

U.S. Pat. No. 6,461,324 B1 discloses a breast shield arrangement having a funnel for receiving a breast of a user and a cylindrical body portion which has a port for applying a vacuum to the outside of the funnel. At the open end of the funnel, a one-way valve is provided.

WO 2018/041365 discloses a breast shield arrangement having a funnel into which the breast is placed. The breast shield arrangement comprises two ports for applying separate vacuums to the breast shield arrangement. One port is arranged at the open end of the funnel and a second port is arranged outside of the funnel.

SUMMARY OF THE INVENTION

It is therefore an object of the invention to provide an improved breast shield arrangement for a breast pump which enables an improved extraction of milk from the breast of the user.

According to an aspect of the invention, a breast shield arrangement for a breast pump is provided. The breast shield arrangement comprises a first sealing portion to seal the breast shield arrangement against a breast of a user. The breast shield arrangement comprises a port which can be coupled to an expression kit or is part of the expression kit such that a vacuum can be applied via the port. The vacuum applied via the port or in the port is the only vacuum in the breast shield arrangement. The breast shield arrangement also comprises an intermediate portion between the first sealing portion and the port. The intermediate portion comprises a circumferentially extending wall which is defining a first volume. The first volume can receive a breast including a nipple and at least part of an areola of a breast of a user. The intermediate portion comprises a first end, a curved portion and a second end. The curved portion comprises a second sealing portion which can seal the curved portion against the breast, e.g. the nipple and at least part of the areola of the user when a vacuum is applied at the port. Thus, a second volume is created between the first sealing portion, the second sealing portion and the breast placed into the intermediate portion. The curved portion in the area of the second volume is curved outwardly from the first portion.

The breast of a user is placed into the intermediate portion which is defining a first volume when no vacuum is applied. When vacuum is applied, the second sealing portion comes into contact with the nipple and/or areola of the user. Hence, the first volume is reduced and a part of the intermediate portion which is not in contact with the nipple or the areola of a user defines a second volume. This volume is limited by the first sealing portion, the second sealing portion and the breast inside the intermediate portion. The second volume is created as the curved portion of the intermediate portion may be at a certain point not fully in contact with the breast of a user. The volume that is enclosed by the curved portion, the first and second sealing portion and the breast of a user corresponds to the second volume. Accordingly, the second volume is a part of the first volume (when no vacuum is applied).

When vacuum is applied, the second sealing portion comes into contact with the breast of the user, e.g. the nipple and may be part of the areola. Depending on the texture of the breast of the user, the second volume may be filled with part of the breast.

By applying the vacuum in or at the port as the only vacuum in the breast shield arrangement and by the arrangement of the intermediate portion, the milk expression is improved.

According to an aspect of the invention, a cross-sectional area of the intermediate portion is continuously reduced from the first end to the second end of the intermediate portion. Preferably, if the intermediate portion is implemented as a funnel, an inner diameter of the funnel is reduced from the first end to the second end of the intermediate portion. In other words, the inner height and width of the intermediate portion is discontinuously reduced. Thus, the intermediate portion can be manufactured easily for example during injection moulding.

The invention also relates to a breast shield arrangement for a breast pump having a sealing portion to seal the breast shield arrangement against a breast of a user, a port and an intermediate portion between the sealing portion and the port. The intermediate portion can receive a part of the breast including a nipple and at least part of an areola of the breast of the user. The intermediate portion has a first end, a curved portion and a second end. The length of the curved portion is greater than a distance between the first and second end of the intermediate portion. The curved portion has a concave shape near the first end of the intermediate portion. A cross-sectional area of the intermediate portion is continuously reduced from the first to the second end of the curved portion.

According to an aspect of the invention, a breast shield arrangement for a breast pump is provided. The breast shield arrangement has a first end as sealing portion for sealing the breast shield arrangement against a breast of a user. The sealing portion is funnel shaped. The breast shield arrangement comprises a second end and a collapsible intermediate portion between the first and second end of the breast shield arrangement. The collapsible intermediate portion has a first end, a curved portion and a second end and is optionally funnel shaped. The first end of the intermediate portion is attached to the sealing portion. The second end of the intermediate portion is attached to the second end of the breast shield arrangement. The length of the curved portion is greater than a distance between the first and second end of the intermediate portion. The curved portion has a concave shape near the first end and a convex shape near the second end of the intermediate portion.

According to an aspect of the invention, a ratio between a diameter of the sealing portion and a total length of the breast shield arrangement is >1 and preferably >1.3. The ratio can also be >1.5 and <3.2. Accordingly, a breast shield arrangement is achieved which has a reduced length.

According to a further aspect of the invention, a ratio between a diameter of the sealing portion and a length of the curved portion of the breast shield arrangement is >1 and preferably >1.3.

According to a further aspect of the invention, the intermediate portion has in a collapsed state a cross section with at least two lopes, preferably three lopes.

According to a further aspect of the invention, a wall thickness of the curved portion is substantially constant.

According to a further aspect of the invention, the curved portion comprises a first and second end as well as a first and second curved section. The first and second end of the curved portion correspond to the first and second end of the intermediate portion, respectively. The first and/or second curved section corresponds to a first contact point being a first point of contact with a nipple of a user when a vacuum is applied to the breast shield arrangement and the intermediate portion collapses.

According to a further aspect of the invention, the breast shield arrangement comprises a support structure which is at least partly surrounding the sealing portion and the intermediate portion. The support structure is made of a rigid material. The sealing portion and the intermediate portion form an insert and are made of a soft and flexible material.

According to a further aspect of the invention, a breast pump is provided which comprises a vacuum pump, a vacuum conduit coupled to the vacuum pump as well as at least one breast shield. The breast shield is coupled to the vacuum pump via the vacuum conduit.

According to an aspect of the invention, the breast shield arrangement for the breast pump comprises a funnel configured to receive a breast of a user. The funnel comprises a sealing portion configured to fit around a breast or a tissue of an areola of a user. The funnel also comprises a collapsible portion configured for nipple and/or areola stimulation and a contact point of a first contact of the collapsible portion on a nipple of a user.

According to an aspect of the invention, the sealing portion is independent from the collapsible portion in such a way that the sealing portion can be pressed against the areola or the breast of the user before the collapsible portion of the funnel is pressed against the nipple of the user. In particular, the collapsible portion of the funnel is brought in contact at a contact point at the nipple of the user. In other words, the first point of contact is at the nipple of the user and not at the areola or the breast of a user at least regarding the collapsible portion of the funnel.

According to an aspect of the invention, a method of operating a breast shield arrangement for a breast pump is provided. The breast shield arrangement comprises a first end as a first sealing portion, a port and an intermediate portion between the sealing portion and the port. The intermediate portion comprises a circumferentially extending wall defining a first volume into which a breast of a user is placeable. The intermediate portion has a curved portion. The intermediate portion is placed over a nipple and at least part of an areola of a breast of a user. The breast shield arrangement is sealed against a breast of a user by the first sealing portion at the first end of the breast shield arrangement. The port of the breast shield arrangement is coupled to an expression kit or is part of the expression kit and a vacuum is applied at the port of the breast shield arrangement by a vacuum pump such that a second sealing portion of the curved portion is brought into contact against a nipple and/or at least part of the areola of a breast. The vacuum in or at the port is the only vacuum in the breast shield arrangement. A second volume is created between the first and second sealing portion as well as the areola or the breast of a user. The curved portion at the second volume is curved outwardly.

According to an aspect of the invention, the breast shield arrangement for the breast pump can be operated at least in a stimulation mode (resulting in a Milk Ejection Reflex MER) and an expression mode (resulting in a milk expression).

According to an aspect of the invention, when no vacuum is applied, the intermediate portion is configured such that a nipple of a user can be inserted without coming into contact with the curved portion.

According to an aspect of the invention, a computer program for operating a breast pump is provided. The computer program comprises program code means for causing a breast pump to carry out the steps of the method of operating a breast pump when the computer program is run on a computer controlling the breast pump.

It shall be understood that a preferred embodiment of the present invention can also be any combination of the dependent claims or above embodiments with the respective independent claim.

These and other aspects of the invention will be apparent from and elucidated with reference to the embodiments described hereinafter.

BRIEF DESCRIPTION OF THE DRAWINGS

In the following drawings:

FIG. 8 shows a schematic cross section of a breast shield arrangement illustrating typical problems, FIGS. 14A to 14C show schematic cross sections of a breast shield arrangement and a breast during the extraction of milk according to an aspect of the invention, FIGS. 18A to 18E show schematic cross sections of a breast shield arrangement during the operation of the breast shield arrangement, FIG. 19 shows a schematic cross section of a breast shield arrangement according to an aspect of the invention, FIG. 20 shows a schematic cross section of a breast shield arrangement according to an aspect of the invention.

DETAILED DESCRIPTION OF EMBODIMENTS

Figure 1A:
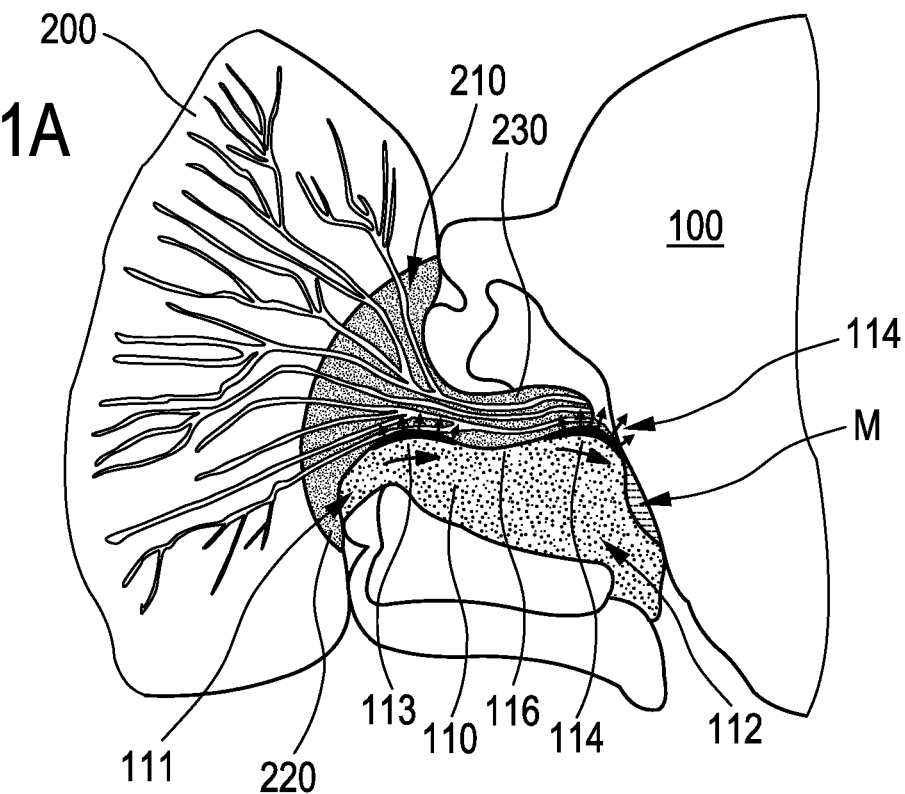
FIGS. 1A and 1B show schematically and exemplary a general anatomy of the sucking of an infant.
Figure 1B:
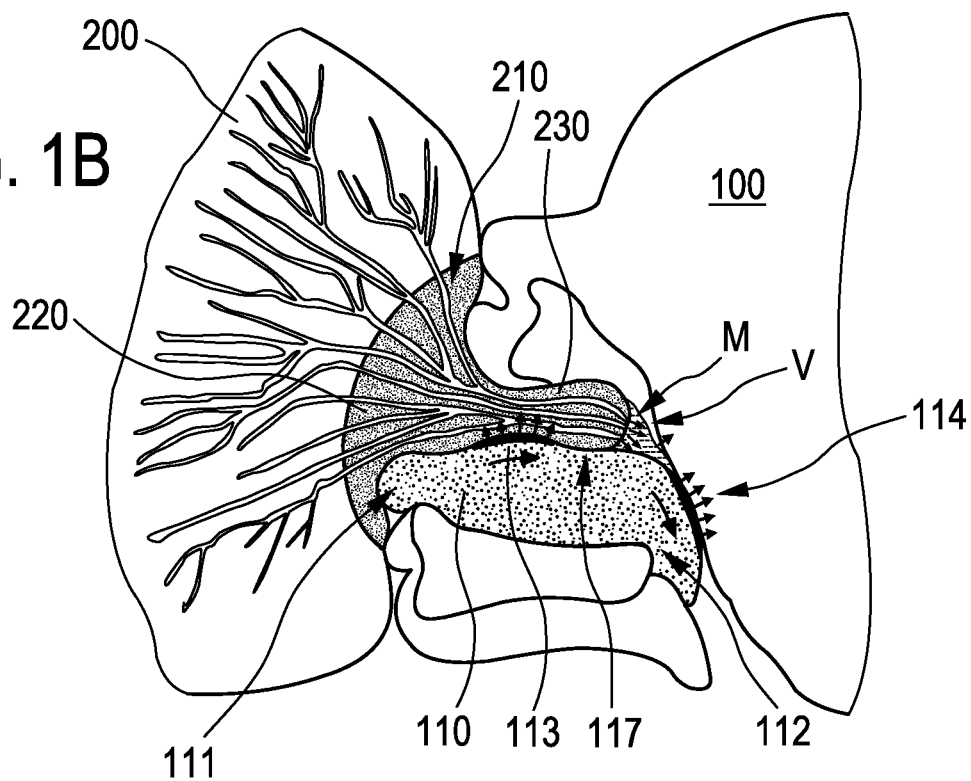
Figure 2:
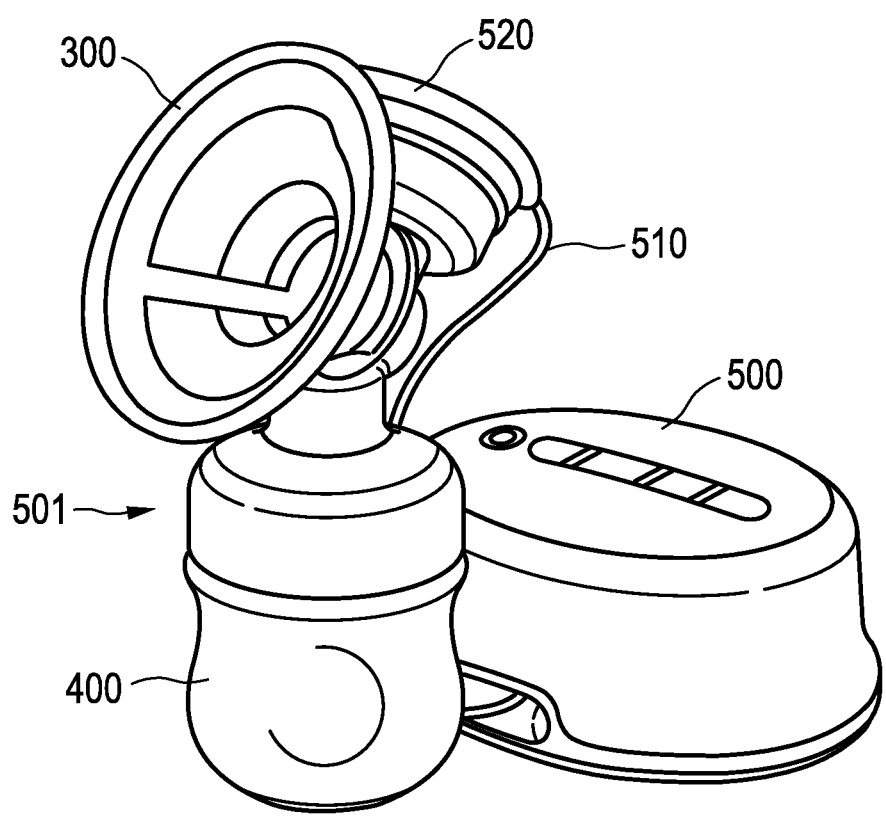
FIG. 2 shows a schematic set up of a breast pump according to an aspect of the invention.

FIG. 2 shows a schematic set up of a breast pump according to an aspect of the invention. The breast pump comprises an expression kit 501 to which a funnel shaped breast shield 300 is coupled, optionally a bottle 400 as well as a vacuum generating unit like a vacuum pump 500 and a vacuum conduit 510. When the breast of the user is placed into the breast shield 300 and the pump 500 is switched on, the vacuum pump 500 will create a vacuum in the breast shield 300 and part of the expression kit 501 via the conduit 510. Thus, the extraction of milk can be performed. The milk extracted from the breast will flow into the bottle 400.

Alternatively, a vacuum unit 500 generating a vacuum can be coupled directly to the expression kit.

Optionally, the vacuum pump can be operated between 0 and −400 mbar. The vacuum pump can be operated in a first operating mode at −150 mbar, in a second operating mode at −225 mbar, in a third operating mode at −275 mbar and in a fourth operating mode at −333 mbar. The vacuum rates can be at −75 up to −800 mbar/s.

The breast shield 300 comprises according to an aspect of the invention a hard support frame and a flexible insert. The insert can be of a flexible material such that it collapses if a vacuum is applied to the breast shield. The insert can be optionally funnel-shaped. A cross-sectional area of the insert is reduced between its first end to its second end, wherein a breast of a user is received at a first end of the insert. The insert comprises a first sealing portion which is used to seal against a breast of a user when the breast is inserted into the insert and a vacuum is applied. If a vacuum is applied, the insert can collapse if it is made from a flexible material.

Figure 3:
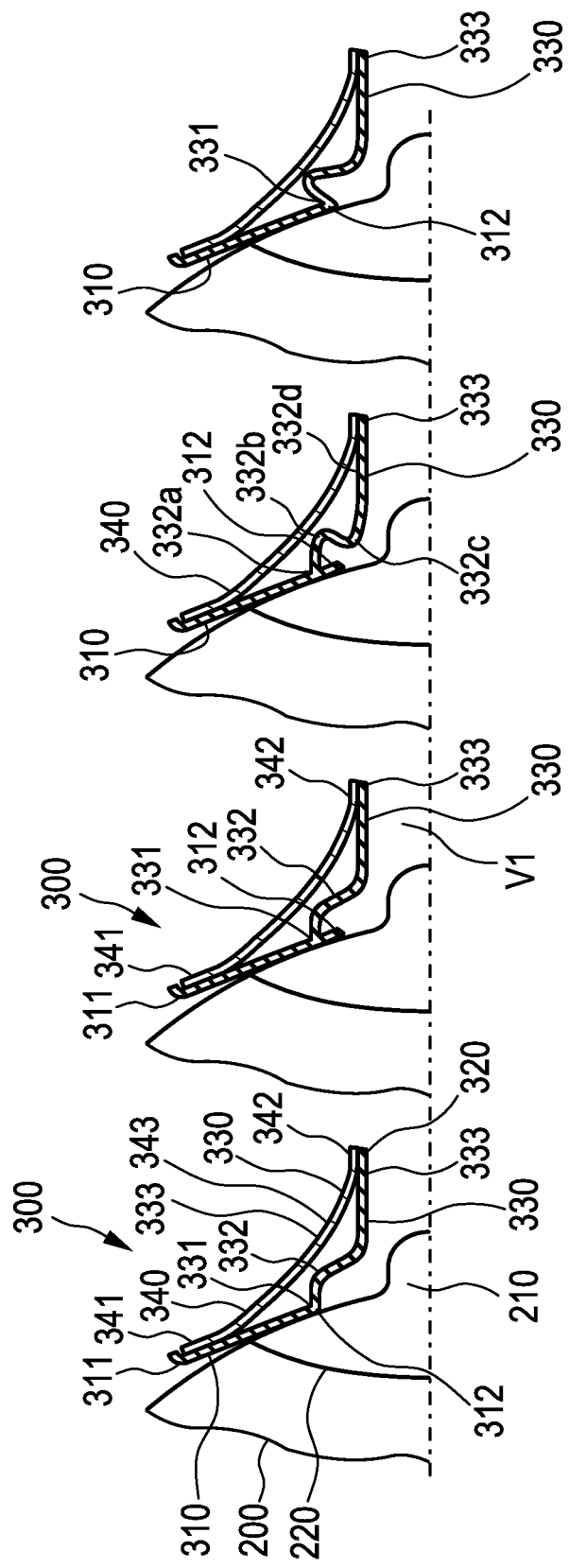
FIG. 3 shows a schematic cross section of a breast shield arrangement according to an aspect of the invention.

FIG. 3 shows a schematic cross section of a breast shield arrangement according to an aspect of the invention. In FIG. 3, a breast 200 having an areola 220 and a nipple 210 are depicted which is placed inside a volume V1 defined by a breast shield 300. The breast shield 300 may comprise a support frame or structure 340 made from a hard material as well as an insert 310, 320, 330. The insert is preferably made from soft material like soft silicon. The insert comprises a first end which acts as a sealing portion 310. The insert also comprises a second end. The first end of the breast shield 300 is designed to receive a breast 200 of a breast feeding woman. Through the second end or port 320 of the breast shield 300, the extracted milk can flow into for example a bottle 400 as shown in FIG. 2.

The insert also comprises an intermediate portion 330 between the sealing portion or the first end 310 and the second end 320 of the breast shield 300 which can serve as a port to couple the breast shield to an expression kit.

The sealing portion 310 comprises a first end 311 and a second end 312. The second end 312 of the sealing portion 310 is placed against the areola 220 or the breast 200 of a user as shown in FIG. 3 depending on the size of the areola.

Thus, the breast 200 is shielded against the outside atmosphere so that a vacuum can be created in the volume defined by the breast 200 of a user and the surrounding intermediate portion 330.

According to the invention, the support frame 340 comprises a first end 341 and a second end 342. The first end 341 is in contact with the first end 311 of the sealing portion 310. The second end 342 is in contact with the second end 320 of the breast shield 300. In other words, the rest of the insert, in particular the intermediate portion 330, is typically not in contact with the support frame or structure 340.

The intermediate portion 330 is designed to collapse when a vacuum is applied. In this case, the intermediate portion 330 will adhere to or surround the nipple 210 of the user.

Preferably, the support frame or structure 340 is implemented as a hard plastic body part which should be stiff and can provide support for the insert. The sealing portion 310 of the insert together with the first end 341 of the support structure 340 can implement a sealing function to enable a vacuum in the volume defined by the nipple of the user and the intermediate portion 330. Preferably, the sealing portion 310 of the insert is placed at least partly against the areola or the breast of the user such that the nipple is typically not in contact with the sealing portion 310 when the breast shield 300 is placed over the breast 200 of a user. In particular, the intermediate portion 330 can be implemented such that when it is collapsing due to an applied vacuum, the collapsing intermediate portion will first touch the nipple before it touches the areola. Furthermore, preferably the intermediate portion 330 is implemented such that the surface of the nipple is supported during a vacuum cycle. Preferably, the insert is made of soft silicon and is flexible such that it allows a collapsing behavior.

According to the invention, the function of the sealing portion 310 is decoupled from the function of the collapsible intermediate portion 330. In other words, when the breast 200 of a user is placed into the breast shield 300 (this means when no vacuum is applied yet), the sealing portion 310 will come to rest against the breast, e.g. the areola or the breast while the collapsible intermediate portion 330 is not fully in contact (i.e. not fully circumferentially in contact) with the areola 220 or the nipple 210 as can be seen in FIG. 3. The collapsible intermediate portion 330 will only then come into contact first with the nipple 200 and then possibly with the areola 220 when a vacuum is applied to the breast shield 300. In that case, the intermediate portion 330 will collapse and will first come in contact with the nipple 210 and only thereafter with the areola 220 of the user.

According to the invention, the sealing function implemented by the sealing portion 310 is decoupled from the collapsible intermediate portion 330 by providing the intermediate portion 330 with a curved design which can be a trapped design, a S-shaped design, a C-shaped design or any other design which enables an increase of the length of the intermediate portion in the axial direction and therefore a greater displacement in radial direction.

As shown in FIG. 3, the intermediate portion 330 has a first end 331 which is coupled with the sealing portion 310. The intermediate portion 330 furthermore comprises a second end 333 which is arranged at the second end 320 of the breast shield 300. In between the first and second end 331, 333, the curved portion 332 is present. The intermediate portion 330 comprises a first end 331, a second end 333 and a curved portion 332 in between the first and second end 331, 333. In other words, the length of the curved portion 332 is greater than a distance between the first and second ends of the intermediate portion. The curved portion 332 comprises a first end 332a, a second end 332d and optionally a first and second curved section 332b, 332c between the first and second end 332a, 332d In the left hand picture in FIG. 3, the first end 331 of the intermediate portion 330 is coupled to the second end 312 of the sealing portion 310. In the second picture, the first end 331 of the intermediate portion 330 is coupled to the sealing portion 310 at a predetermined distance from the second end 312. In the third picture, the first end 331 is coupled to the sealing portion 310 at a predetermined distance from the second end 312 of the sealing portion 310. In the fourth picture, the second end 312 of the sealing portion 310 is coupled to a first end 331 of the intermediate portion 330.

Depending on the length of the intermediate portion 330 and in particular the curved portion 332, at least a first and second curved section 332b, 332c is present.

When a vacuum is applied to the breast shield by means of the vacuum pump 500 and when the pressure inside a volume defined by the breast and the breast shield (namely the intermediate portion 330) is sufficiently smaller than the atmosphere outside the intermediate portion 330 (e.g. the atmosphere pressure) the intermediate portion 330 will collapse and come into contact with the areola 220 and the nipple 210.

Figures 4A, 4B:
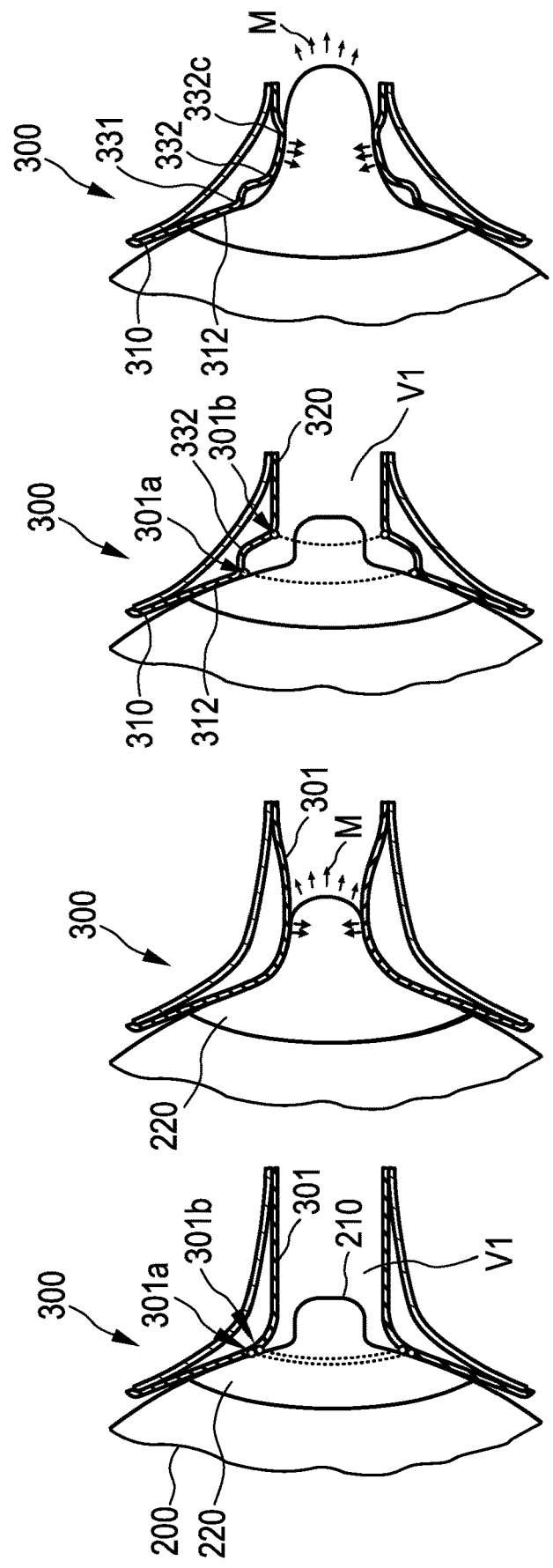
FIG. 4A shows a schematic cross section of a conventional collapsible breast shield arrangement.
FIG. 4B shows a schematic cross section of a breast shield arrangement according to an aspect of the invention.

FIG. 4A discloses a schematic cross section of a conventional collapsible breast shield arrangement and FIG. 4B shows a schematic cross section of a breast shield arrangement according to an aspect of the invention. When the breast 200 of a user is placed into the conventional breast shield 300, the areola 220 is pressed against a flexible insert 301. A position 301a at which the breast and/or areola is sealed by the breast shield corresponds to the first point of contact 301b after the collapse of the funnel as shown in the right hand picture of FIG. 4A. Only thereafter, the rest of the flexible insert 301 comes into contact with the nipple 210 of the user.

In FIG. 4B, however, the sealing of the breast 200 or areola 220 will take place at a position corresponding to the second end 312 of the sealing portion 310 when the breast 200 is placed into a volume V1 defined by the breast shield 300. Due to the curved portion 332, the first point of contact after the collapse of the intermediate portion 330 will correspond to a first or second curved section 332b, 332c. This is in particular shown in the right hand picture of FIG. 4B. Here, first the intermediate portion 330, namely in particular the curved portion 332, comes into contact with the nipple 210 before the rest of the intermediate portion 330 and in particular the first end 332a of the curved portion 332 comes into contact with the areola 220 or the nipple 210.

This is in particular advantageous as it enables an improved extraction of milk M as it simulates the sucking motion of a baby.

Figure 5:
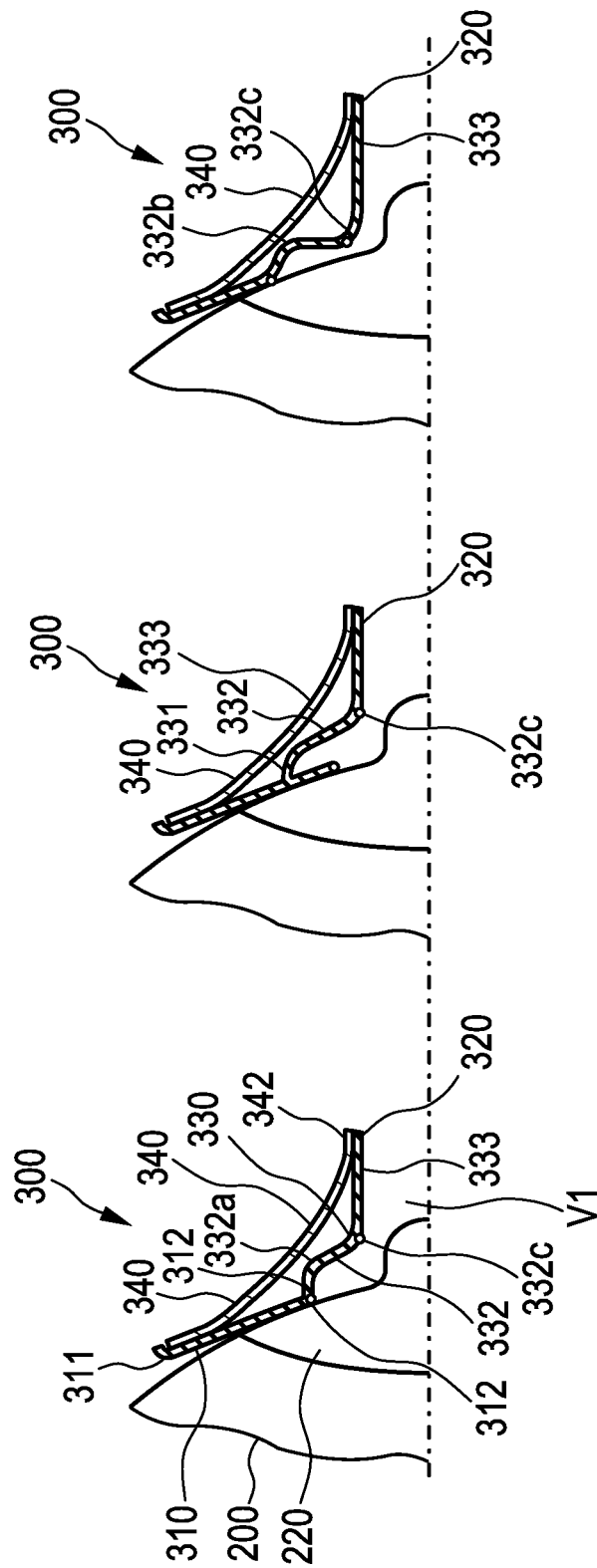
FIG. 5 shows a schematic cross section of a breast shield arrangement according to an aspect of the invention.

FIG. 5 shows a schematic cross section of a breast shield arrangement according to a further aspect of the invention. The breast shield 300 defines a volume V1 and comprises a sealing portion 310 having a first and second end 311, 312 as well as an intermediate portion 330. Furthermore, a curved portion 332 of the intermediate portion 330 is provided between the second end 312 of the sealing portion 310 and the second end 320 of the breast shield 300. The curved portion 332 comprises a length which is greater than the distance between the second end 312 of the sealing portion 310 and the second end 320 of the breast shield. Thus, the intermediate portion 330 has a curved design. Depending on the length of the curved portion 332, a first and second curved section 332b, 332c is more or less prominent. Because of the curved portion 332 which first end 332a is coupled to the second end 312 of the sealing portion 310 or which is coupled at a predetermined distance from the second end 312, the first point of contact of the intermediate portion 330 with the nipple 210 or the areola 220 when vacuum is applied can correspond to the second curved section 332c. Thus, the first point of contact of the intermediate portion 332 with the nipple 210 or the areola 220 will not be close to or in the proximity of the sealing portion 310.

The design of the intermediate portion 330 with the curved portion 332 according to an aspect of the invention is advantageous as it enables a tactile stimulation of the erectile portion of the nipple or the areola is touched by the intermediate portion 330. Such a nipple stimulation is advantageous to initiate a Milk Ejection Reflex MER. According to an aspect of the invention, by the particular arrangement of the intermediate portion 330 and the curved portion 332 and by applying a vacuum, the collapsible intermediate portion 330 will collapse on the nipple before the intermediate portion 330 reaches the areola. This is advantageous as vacuum remains to be applied on the areola which allows a proper expansion of the milk ducts so that they can fill with produced milk from the milk glands.

Figure 6:
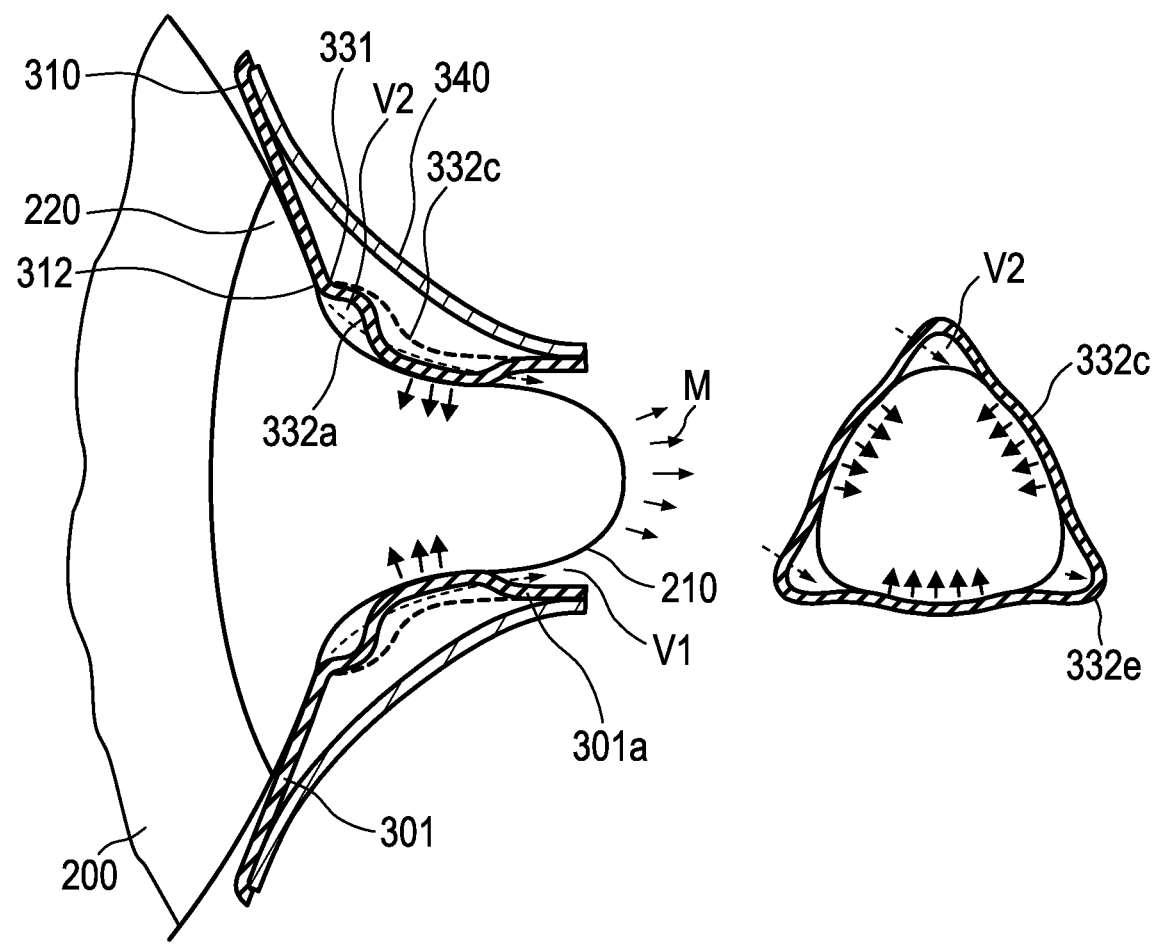
FIG. 6 shows a schematic cross section of a breast shield arrangement according to an aspect of the invention.

FIG. 6 shows a schematic cross section of a breast shield arrangement according to a further aspect of the invention. In FIG. 6, an intermediate step during the creation of the vacuum is depicted in order to extract milk M from the breast 200 of a user. A breast 200 is placed into a first volume V1 defined by the breast shield 300. Here, the curved portion 332 and in particular the second curved section 332c is in contact with the nipple 210 of the user. While the second curved section 332c is in contact with the nipple 210, the section 332e is not in contact such that a second volume V2 is created between the first sealing portion 310 and a second sealing portion 332c defined by the point of contact between the nipple 210 and the curved section 332c.

Figure 7:
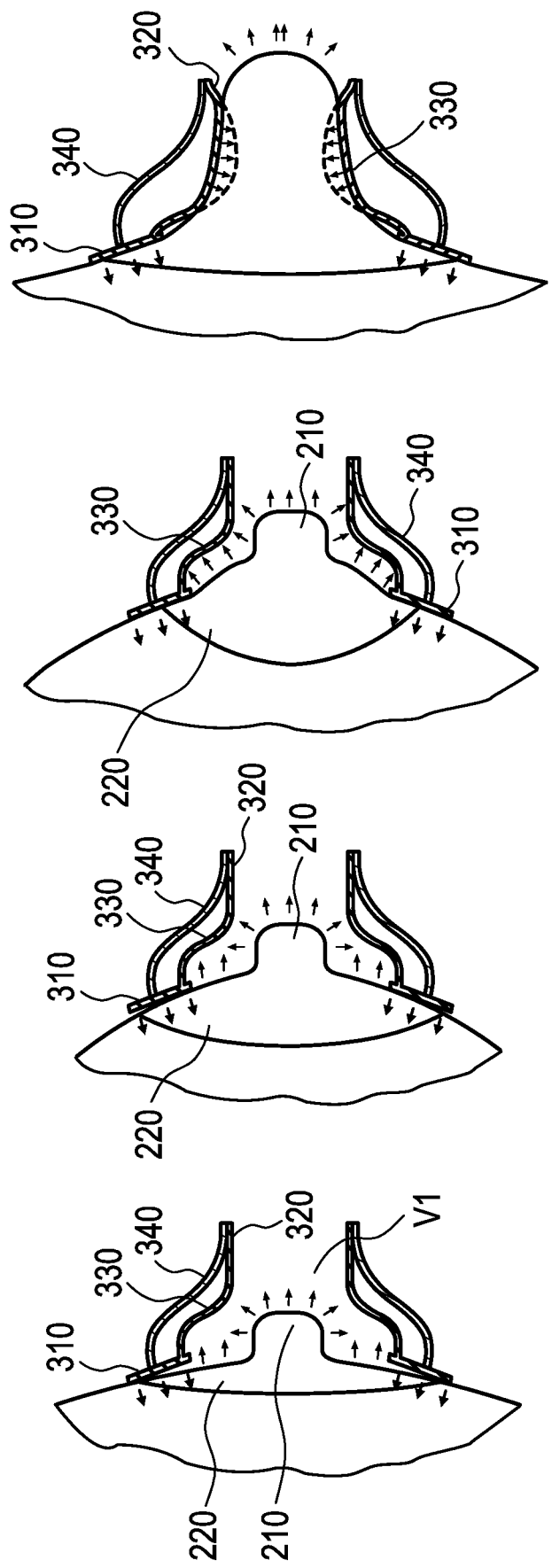
FIG. 7 shows a schematic cross section of a breast shield arrangement according to a further aspect of the invention.

FIG. 7 shows a schematic cross section of a breast shield arrangement according to a further aspect of the invention. In FIG. 7, the different steps are depicted when the breast shield 300 is placed against a breast of a user such that the breast 200 is placed into a volume V1 and the vacuum is applied. First of all, the sealing portion 310 will be placed against the areola 220 or the breast of the user. Then when vacuum is applied, the collapsible intermediate portion 330 will collapse and come into contact with the nipple 210 or areola of the user before the intermediate portion 330 is in contact with the rest of the breast of the user. With the breast shield arrangement according to the invention, it is possible to simulate a natural pumping which corresponds to the sucking of a baby. This is achieved by stimulating the milk let-down by firstly the nipple 210 comes into contact with the intermediate portion 330 before the areola is touched by the intermediate portion 330. It should be noted that of course the sealing portion 310 must first come in contact with the areola and the breast of the user such that a vacuum can be generated. However, the collapsible intermediate portion 330 comes first into contact with the nipple 210 and only thereafter with the areola 220. This is advantageous as the nipple 210 is compressed and supported while forming a teat avoiding overstretching or rubbing. The breast shield 300 according to the invention is advantageous as it fits to substantially every nipple size.

FIG. 8 shows a schematic cross section of a breast shield arrangement according to the prior art illustrating typical problems. In prior art breast shield arrangement as shown in FIG. 8, problems may occur when the breast is firm or the nipple is small leading to a tissue stretching as shown in the two figures at the top of FIG. 8. On the other hand, if the nipples 210 are too large to fit the funnel, this can lead to a rubbing of the nipple against the funnel as shown in the two bottom Figures of FIG. 8.

Figure 9A:
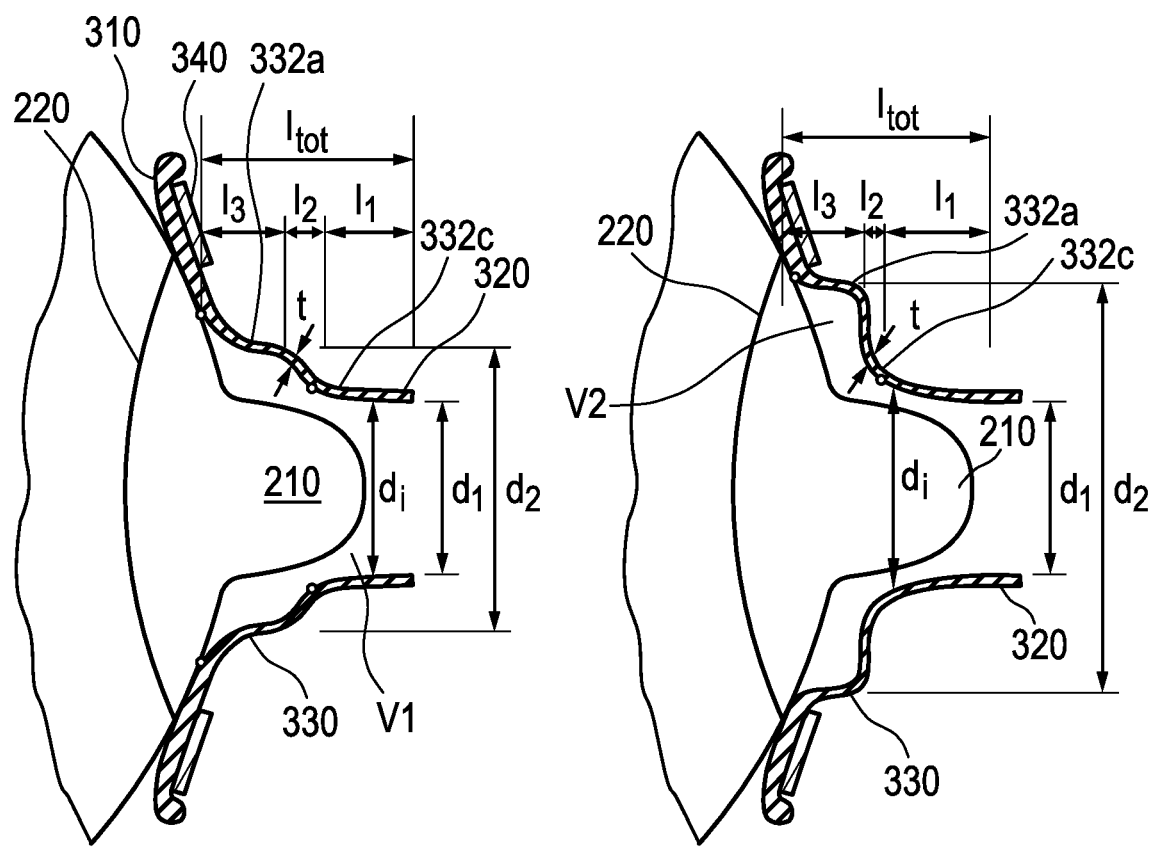
FIG. 9A shows a schematic cross section of a breast shield arrangement according to a further aspect of the invention.

FIG. 9A shows a cross section of a breast shield arrangement 300 according to a further aspect of the invention. The breast 200 of the user is placed into the breast shield. In particular the areola 220 and the nipple 210 are placed into the insert 310, 320, 330. In FIG. 9A, the different parameters of these measurements include the total length $l_{tot}$, a first, second and third length l1-l3, a thickness t and a first and second diameter $d_1$, $d_2$ as well as an inner diameter $d_i$.

The ranges of these parameters are shown in the following table:

| Parameter | Range |
|---|---|
| $d_1$ | 20-25 mm, preferred 22 mm |
| $d_2$ | 30-60 mm, preferred 50 mm |
| $l_{tot}$ | 19-50 mm, preferred 35 mm |
| $l_1$ | 14-20 mm, preferred 17 mm |
| $l_3$ | 5-15 mm, preferred 10 mm |
| $l_2$ | 0-7 mm, preferred 2 mm |
| $l_{func}$ | 19-35 mm, preferred 28 mm |
| t | 0.6-1.4 mm, preferred 1 mm |

The first diameter $d_1$ should be as small as possible to create the most efficient collapse of the collapsible intermediate portion. However, the diameter $d_1$ should as small as possible not be below 22 mm to fit every nipple size tip. The second diameter $d_2$ should be in between 30 and 60 mm and in particular as small as possible not to create an unnecessary dead volume as well as too much forces on the breast. However, the diameter $d_2$ must be large enough to accommodate for substantially every nipple size. Furthermore, the diameter $d_2$ should be large enough to accommodate the curved portion 332 of the collapsible intermediate portion 330. The diameter $d_2$ may also be dependent on how fast the point c touches the nipple-areola complex. The total length $l_{tot}$ should be in between 19 to 50 mm, preferably 35 mm. The total length $l_{tot}$ should be a short as possible, in particular it may correspond to the nipple with respect to the breast in a stretched state, namely about 35 mm. The total length is fixed and is based on no lean forward requirement. The first length $l_1$ should be as large as possible to create a good collapse and to drive in low amounts of lobes. The third length $l_3$ should be long enough to allow a first contact point of collapse at point c but not too long to prevent the complete breast of sucking into the funnel. The second length $l_2$ is a free parameter (e.g. between 0 to 7 mm) and can be used to adapt for the position of point c. The thickness t can be in between 0.6 and 1.4 mm, preferable 1 mm. The thickness can be used to change the collapse in amount of lobes and amount of deflection due to the influence on the stiffness of the intermediate portion.

Figure 9C:
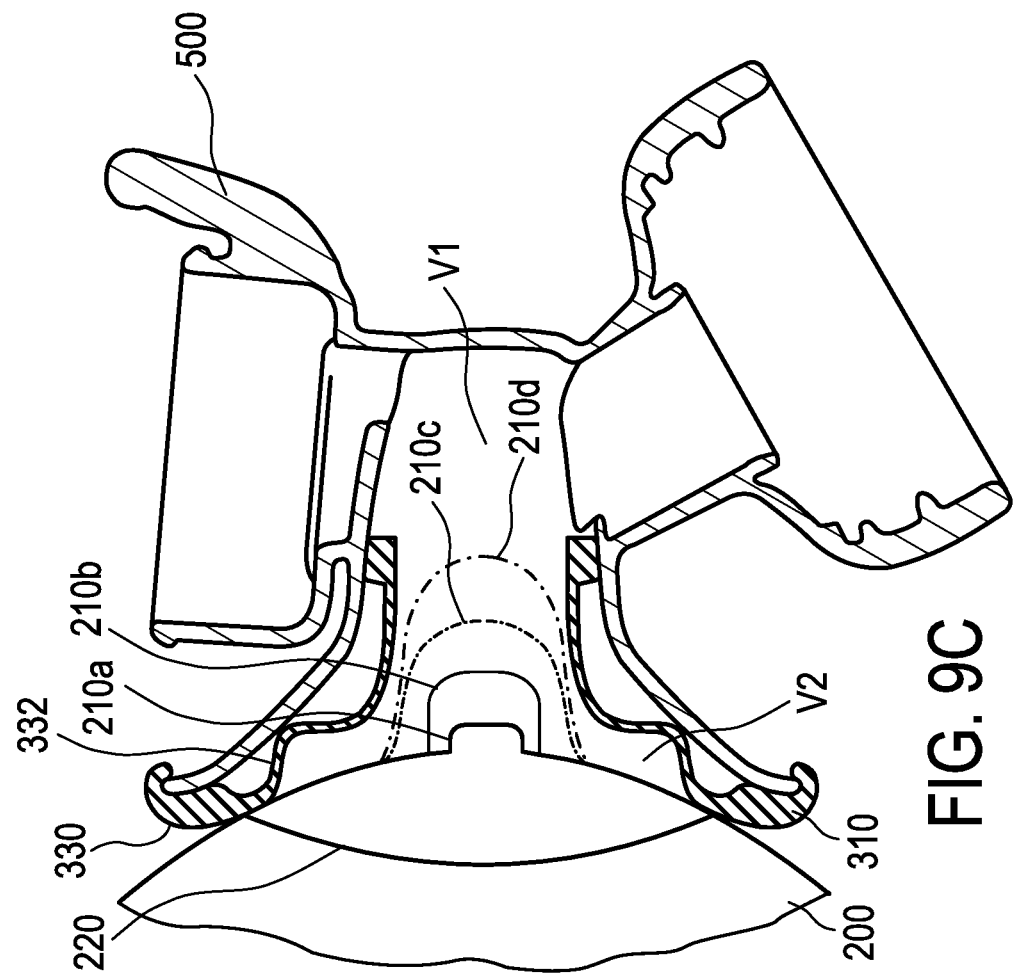
FIG. 9C shows a schematic cross section of a breast shield arrangement and an adapter unit according to a further aspect of the invention.
Figure 9B:
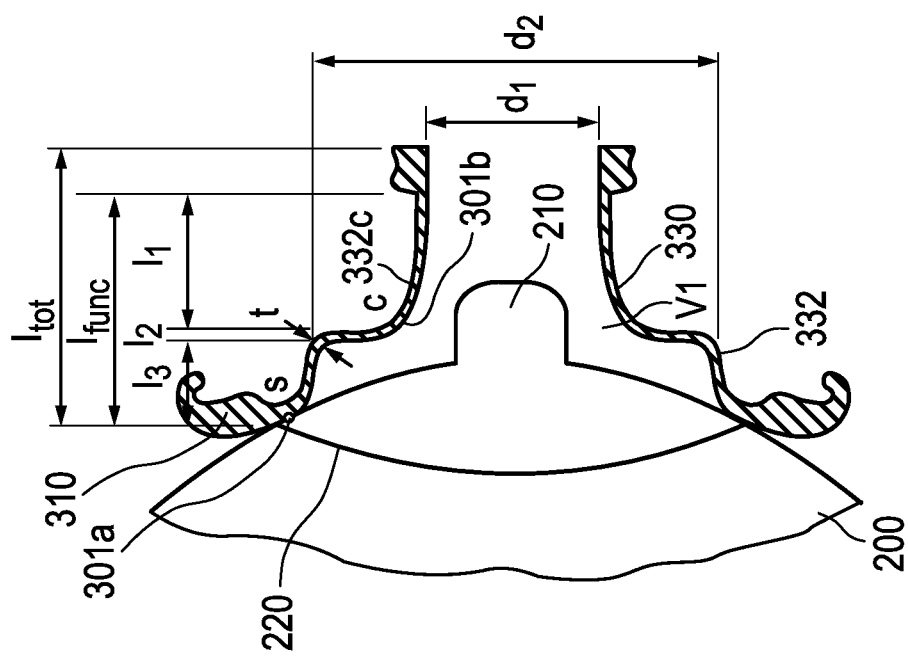
FIG. 9B shows a schematic cross section of a breast shield arrangement according to a further aspect of the invention.

FIG. 9B shows a schematic cross section of a breast shield arrangement 300 according to a further aspect of the invention. A breast 200 of a user is placed into the first volume V1 defined by the breast shield 300. When a vacuum is applied, part of the curved portion 323 comes into contact with the nipple 210 and thus a second volume V2 is created between the first sealing portion 310 and the second sealing portion 332c which is part of the curved portion 332.

FIG. 9C shows a schematic cross section of a breast shield arrangement and an adapter unit according to a further aspect of the invention. Because of the structure of the breast shield 300 and in particular of the insert 310, 320, 330, the breast shield can accommodate a great number of different nipple sizes and nipple shapes. In FIG. 9C a small nipple and an average nipple are shown at the start (small nipple 201a, average nipple 201b), i.e. without any vacuum applied to the breast shield and when vacuum is applied to the breast shield (stretched small nipple 210c, stretched average nipple 210d). The breast shields 300 according to the aspects of the invention fits for substantially all nipple sizes and shape at the start of the operation (no vacuum applied). The breast shield allows that the nipples of virtually all shapes and sizes are touched when the intermediate portion collapses. Thus, the breast shield according to the aspects of the invention is of a one size fits all set-up.

A ratio of the diameter $d_2$ of the sealing portion or the first end 310 of the breast shield and a length of the breast shield is >1 or >1.5 and <3.2.

The intermediate portion 330 and in particular the curved portion 332 of the breast shield arrangement 300 comprises an inner diameter di. This inner diameter di can be continuously reduced between the first and second end of the curved portion 332. A continuously reduced inner diameter of the intermediate portion is advantageous as it allows that the nipple of a user is first touched by the second sealing portion 332c when a vacuum is applied. Accordingly, an intermediate portion will not overlap.

Figure 10A:
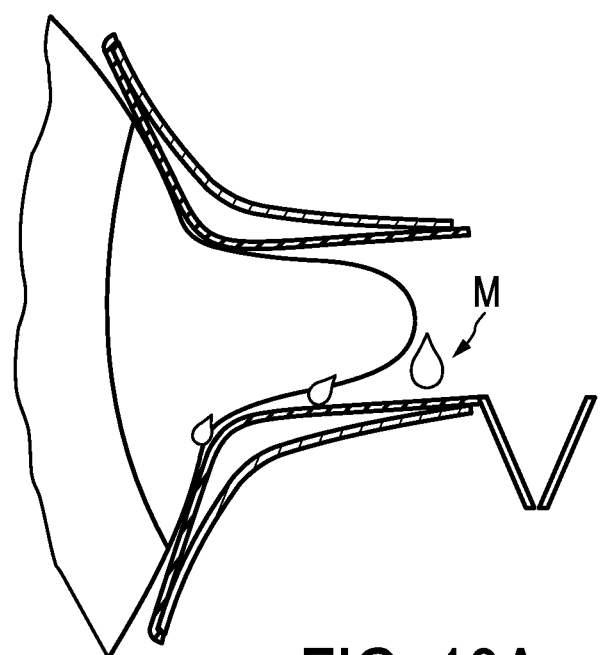
FIG. 10A shows a schematic cross section of a breast shield arrangement according to the prior art.
Figure 10B:
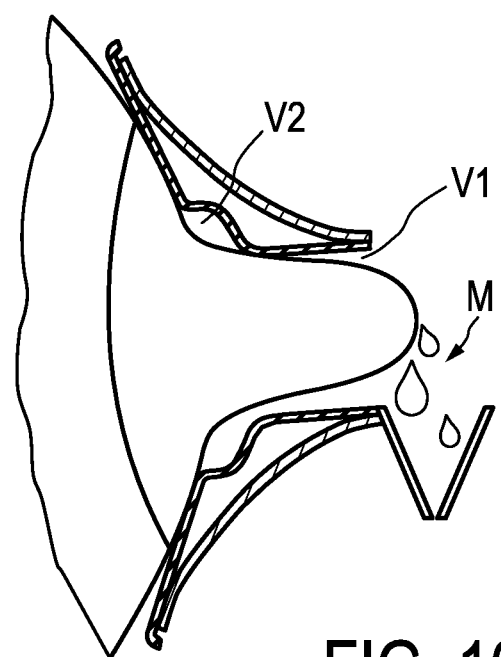
FIG. 10B shows a schematic cross section of a breast shield arrangement according to an aspect of the invention.

FIG. 10A shows a schematic cross section of a breast shield arrangement according to the prior art and FIG. 10B shows a schematic cross section of a breast shield arrangement according to an aspect of the invention. Thus, by implementing a short funnel length, the extracted milk can flow into a container without the need of the breast feeding woman to lean forward. Thus, the breast feeding woman can sit comfortably in a chair or on a sofa in a backward manner while pumping the milk. With the short funnel or breast shield length, it is possible that the milk drops directly above the vertical outlet of the bottle 400 preventing the mother to lean forward during the pumping. This is achieved by the specific ratio of the diameter and the length of the intermediate portion 330 of >1, preferably >1.3 or >1.3 and <3.2, or the curved portion 332. This can furthermore also be achieved by the shape of the curved portion 332 (with its concave and convex section).

The breast shield according to the invention with the short funnel length will still have a good tactile stimulation of the nipple due to the arrangement of the collapsible intermediate portion. The shape of the flexible intermediate portion steps away from the teat contour in order to create a length without increasing the overall length of the membrane.

According to the invention, extra length can be added to increase the collapse. This is advantageous as it is supporting the nipple tissue when high volume is applied thus preventing overstretching. Moreover, it allows more tactile stimulation of the nipples. Moreover, this is also advantageous for small or rigid nipples as the collapsible intermediate portion 330 will also reach these nipples.

Figure 11:
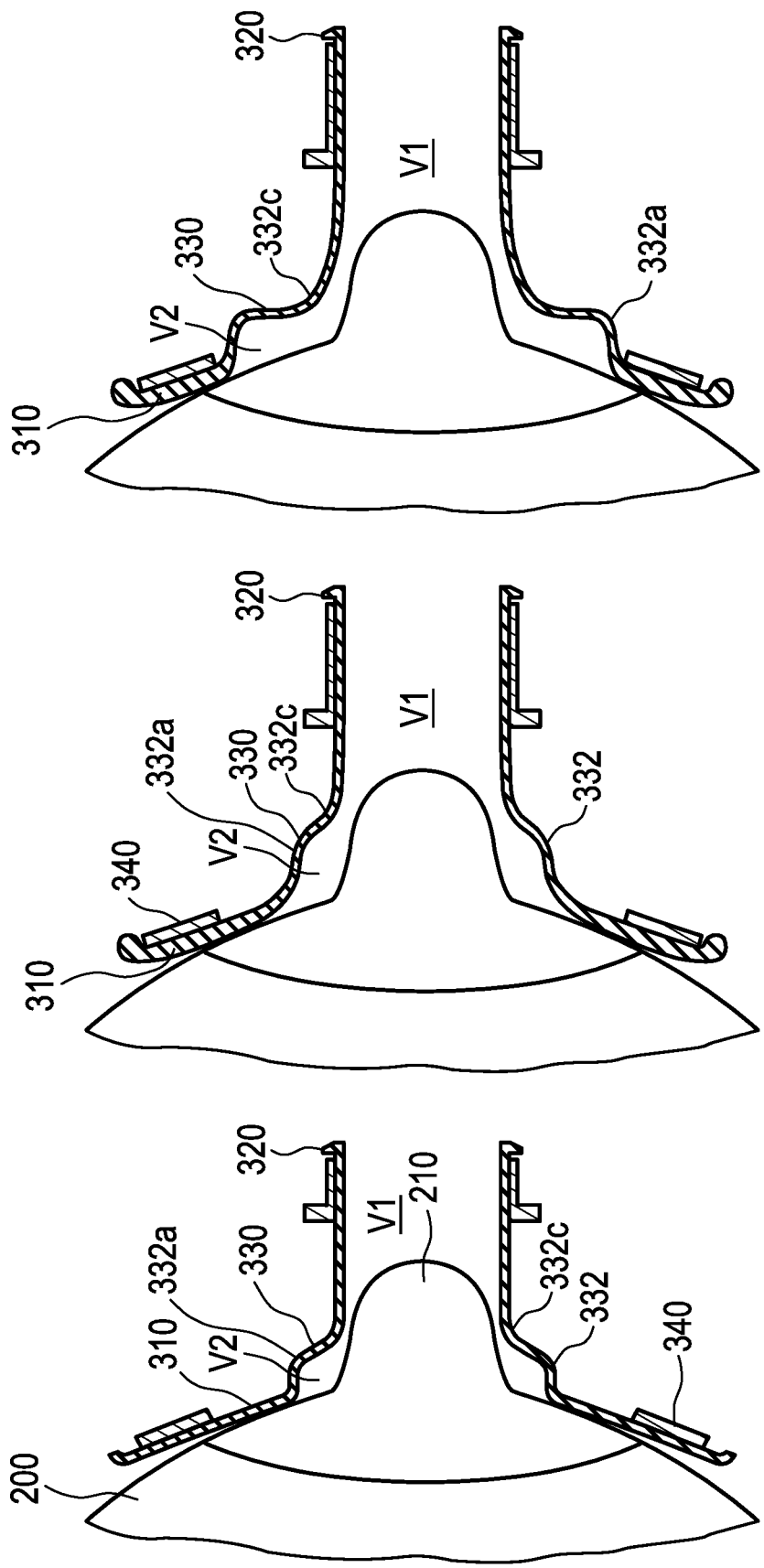
FIG. 11 shows a schematic cross section of a breast shield arrangement according to an aspect of the invention.

FIG. 11 shows a schematic cross section of a breast shield arrangement according to a further aspect of the invention. In FIG. 11, three different arrangements of the collapsible intermediate section are depicted. According to the invention, the curved portion 332 can have a first and second curved section 332a, 332c which can correspond to a first and second lobe. Preferably, the deflection towards the nipple 210 is the largest. Although two curved sections or two lobes are mentioned, the amount of lobes can also be greater than two.

A breast of a user 200 is placed into a first volume V1 defined by the breast shield 300. When a vacuum is applied, a part of the curved portion comes into contact with the nipple 210 such that a second volume V2 is defined between the first sealing portion 310 and a second sealing portion 332c.

Figure 12:
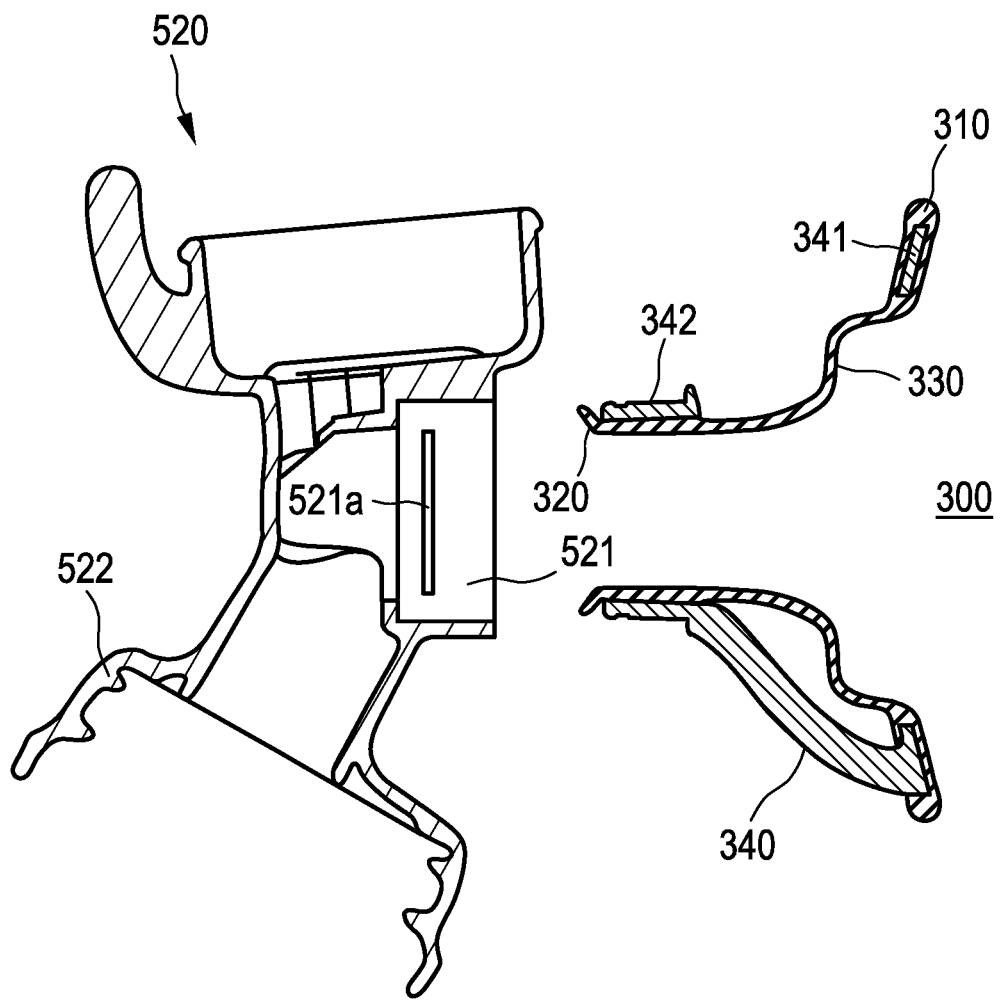
FIG. 12 shows a schematic cross section of a breast shield arrangement and an adapter unit according to a further aspect of the invention.

FIG. 12 shows a schematic cross section of a breast shield arrangement and an adapter unit according to a further aspect of the invention. A breast shield 300 can be placed into an adapter unit 520. The breast shield 300 comprises an insert 310, 320, 330 and a support structure or frame 340. The insert 310, 320, 330 has a function of a suction hood and can be made from soft silicon like liquid silicone rubber. The frame 340 can be made from a hard material like Polybutylene terephthalate (PBT). The frame 340 comprises a first end 341 and a second end 342. The first end 341 is coupled to the first end 310. The frame 340 (in particular a second end 342 of the frame 340) can be fixed or coupled to a first end or port 521 of the adapter unit 520. The insert 310, 320, 330 and the frame 340 can be manufactured as a 2K piece.

Figure 13B:
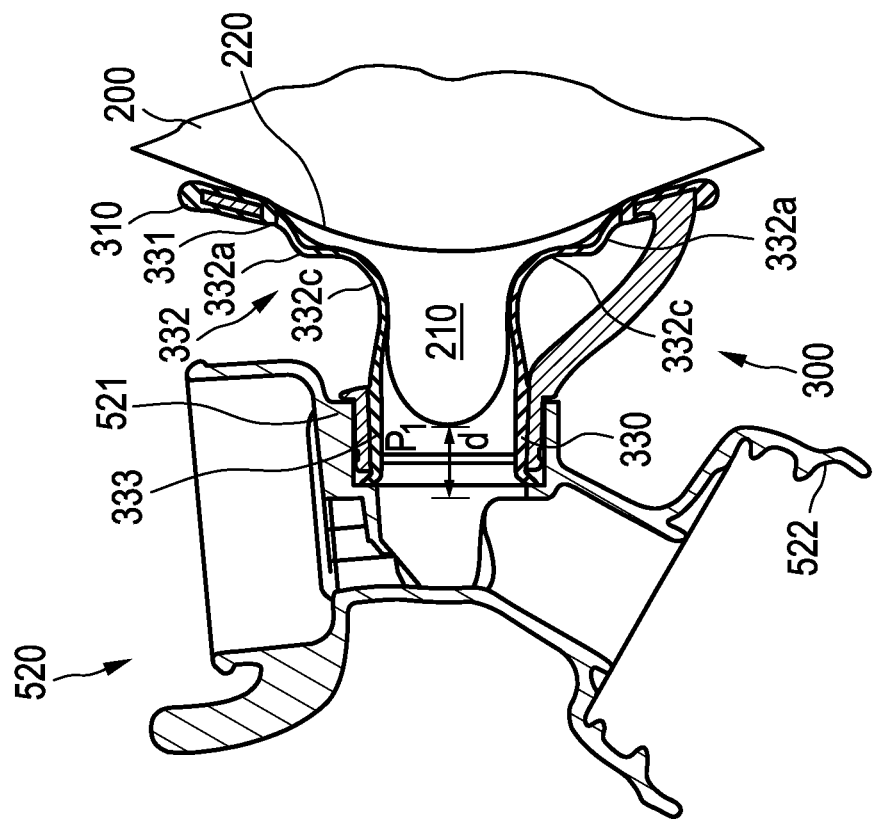
FIGS. 13A and 13B show schematic cross sections of a breast shield arrangement and a breast during the extraction of milk according to an aspect of the invention.
Figure 13A:
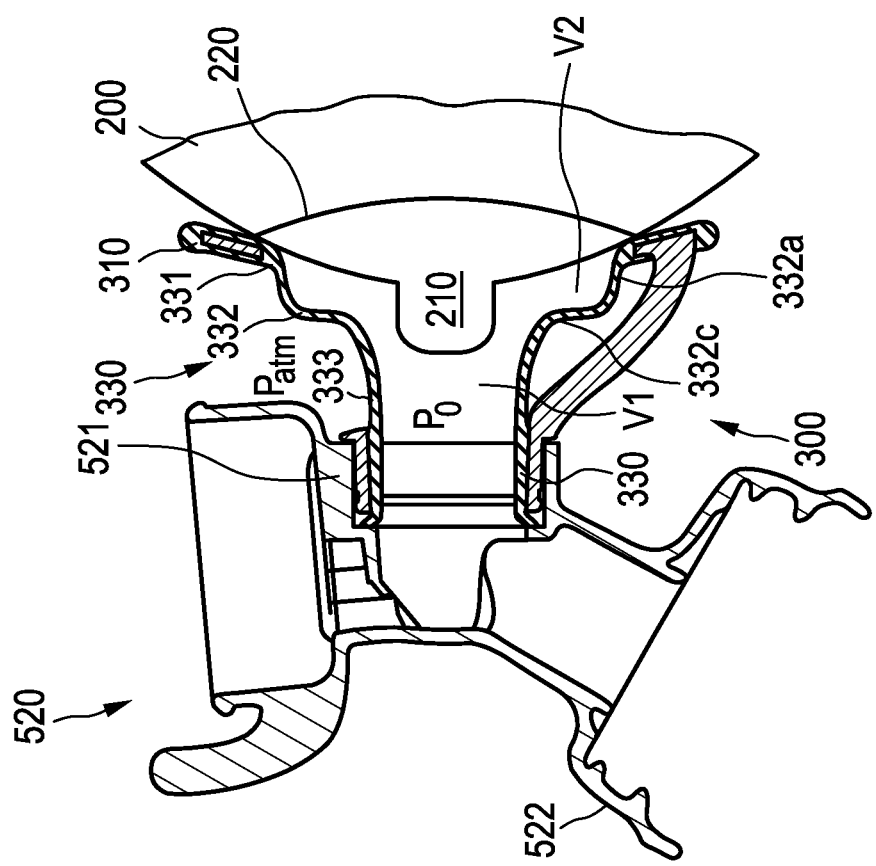

FIGS. 13A and 13B show schematic cross sections of a breast shield arrangement and a breast during the extraction of milk according to an aspect of the invention. FIG. 13A shows the situation when no vacuum is applied to the breast shield 300 and FIG. 13B shows the situation when vacuum is applied to the breast shield 300. Outside the breast shield the atmosphere pressure $P_{atm}$ is present and inside a volume defined by the breast 200 and the breast shield 300 a pressure $P_0$ is present. When a vacuum is applied to the volume defined by the breast 200 and the breast shield 300, the pressure $P_1$ inside the volume will be negative with respect to the atmosphere pressure $P_{atm}$ and thus the intermediate portion 330 and in particular the curved portion 332 made from a soft silicone will collapse or buckle in such that the curved portion 332 touches the nipple 210 and/or the areola 220 and creates a compressive force onto the nipple-areola complex.

The curved portion 332 comprises a first curved section 332a which has a convex shape and a second curved section 332c which has a concave shape. When vacuum is applied and the pressure $P_1$ is below the atmosphere pressure $P_{atm}$, then the curved portion 332 will collapse. In particular, the concave shaped curved section 332c will first come into contact with the nipple 210 before the convex shaped first curved section 332a comes into contact with the areola 220. Thus, the first point of contact of the suction hood with the nipple 210 does therefore not correspond to the sealing portion 310. Accordingly, the sealing portion 310 and the first point of contact 332c between the suction hood and the nipple 210 of the user are decoupled.

Due to the collapse and buckling motion of the curved portion 332, the milk inside the breast will be pushed towards the second end 320 of the breast shield arrangement. Thus, the milk can flow via a second port 522 which can be coupled to a bottle or container. Furthermore, because of the reduced total length $L_{tot}$ of the breast shield arrangement, a distance d between the tip 211 of the nipple 210 and the second port 522 is reduced. This is advantageous as (also described with reference to FIG. 10B) due to the reduced distance d, a user can sit more upright than before. With the design of the breast shield arrangement according to an aspect of the invention, it can be avoided that milk ducts at the tip 211 of the nipples are closed.

As shown in FIGS. 13A and 13B, the breast shield arrangement 320 can be introduced or coupled to the first end or port 521. The breast shield arrangement 300 comprises the support structure or frame 340 and the flexible insert 310, 320, 330.

A breast of a user 200 is placed into a first volume V1 defined by the breast shield 300. When a vacuum is applied, a part of the curved portion comes into contact with the nipple 200 such that a second volume V2 is defined between the first sealing portion 310 and a second sealing portion 332c.

FIGS. 14A to 14C show schematic cross sections of a breast shield arrangement and a breast during the extraction of milk according to an aspect of the invention. The breast shield arrangement and the adapter unit according to FIG. 14A 14C have a slightly different design than the breast shield arrangement and the adapter unit of FIG. 13A 13B. In particular, the support structure or frame 340 can be part of the expression kit 501 such that the support structure or frame 525 can have a funnel shape and can be coupled to the expression kit. In other words, the support structure or frame 525 can be manufactured with the rest of the expression kit 502 in one piece. The flexible insert 310, 320, 330 can be placed into the support structure and frame 340 such that the sealing portion 310 is arranged at the outer end of the support structure or frame 340. In FIG. 14A, the expression kit and breast shield arrangement are disclosed before the operation. In FIG. 14B, the situation is disclosed where no vacuum is applied to the breast shield arrangement. A breast 200 of a user is placed into a first volume V1 which is defined or enclosed by the breast shield arrangement. In FIG. 14C, a vacuum is applied to the breast shield arrangement 300 and the nipple 210 of the breast 200 of the user is stretched towards the second end 320 of the breast shield arrangement 300. The intermediate portion 330 comprises a first concave shaped curved section 332a and a second convex shaped curved section 332c (as seen from the first end 310 or as seen from a breast inside the breast shield). When a vacuum is applied to the breast shield arrangement, the collapsible intermediate portion and in particular the collapsible curved portion 332 will collapse such that the concave curved section 332 comes into contact with the nipple (and possibly the areola) of the user before the first concave shaped curved section 332a comes into contact with the nipple or the areola. Accordingly, between the first sealing portion 310 and a second sealing portion 332c, the wall 330b of the intermediate portion 330 is at least partly not in contact with the areola 220 of the user thus creating a second volume V2.

Figure 15A:
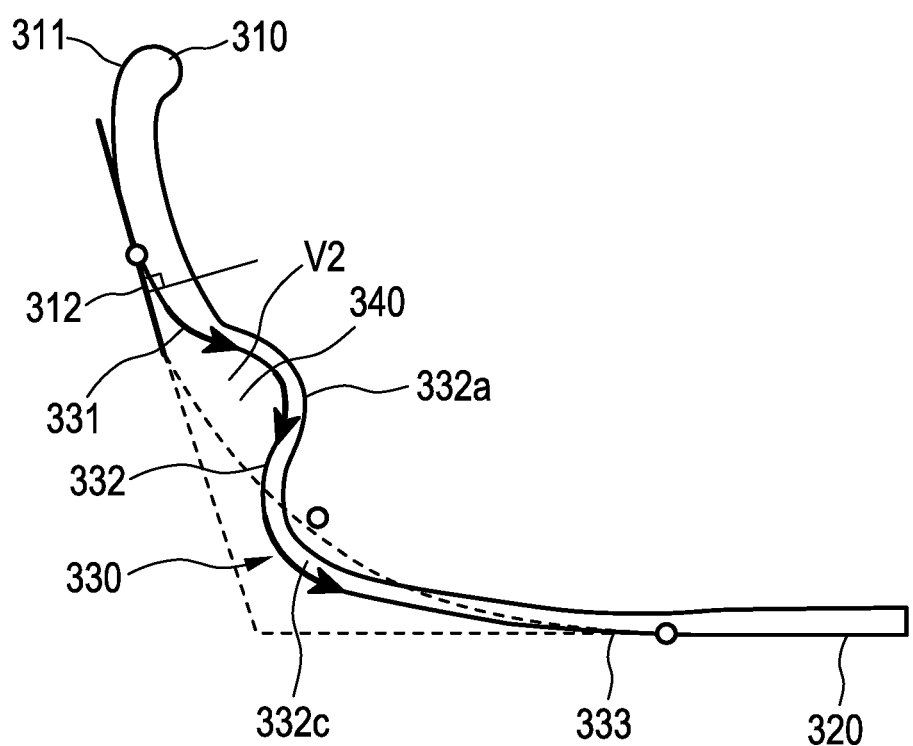
FIGS. 15A to 15C show schematic cross sections of a curved portion of the intermediate portion.
Figure 15B:
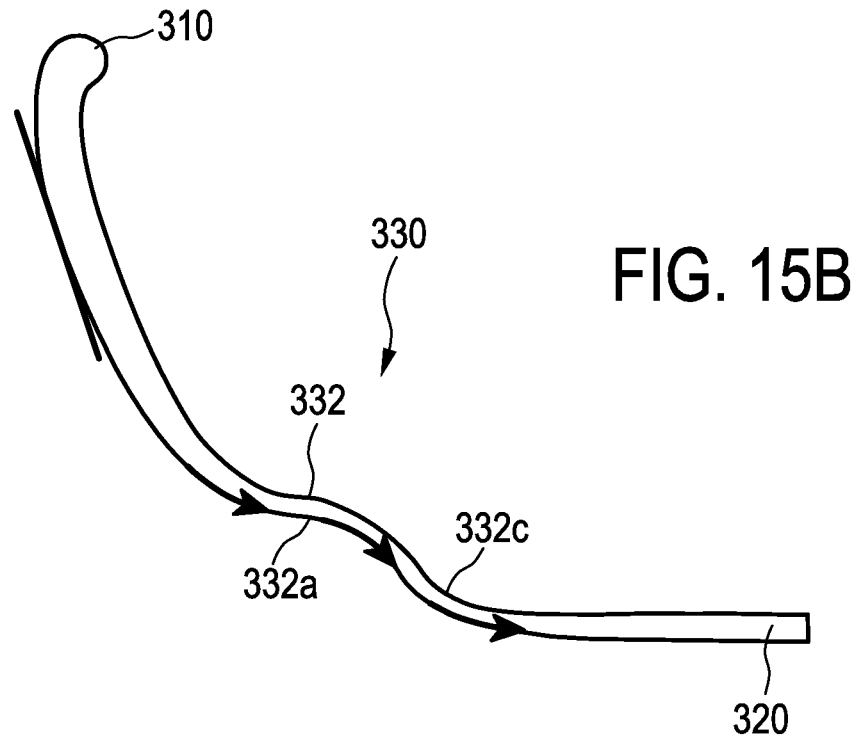
Figure 15C:
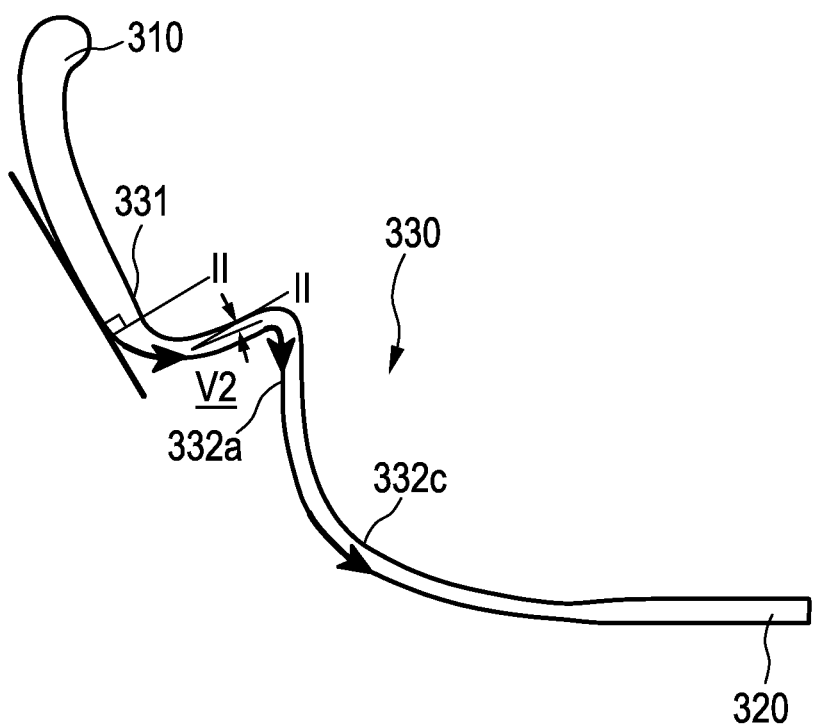

FIGS. 15A to 15C show schematic cross sections of a curved portion of the intermediate portion. The intermediate portion 330 of the breast shield arrangement 300 according to an aspect of the invention comprises a first end 331 followed by a concave portion or section 332a which is again followed by a convex portion or section 332c and a second end 333 of the collapsible intermediate portion 330. Accordingly, the intermediate portion 330 has a shape with a double curvature. In the FIGS. 15A 15C, an intermediate portion 330 with different curvatures is depicted. The first end 310 of the intermediate portion 330 is implemented as a sealing portion 310 which is pressed against the breast of a user. The sealing portion 310 comprises a first and second end 311, 312. Between the sealing portion 311 and the second end 320, the intermediate portion 330 is provided. A first end 331 of the intermediate portion 330 is coupled to the second end 312 of the sealing portion 310. Between the first and second end 331, 333 of the intermediate portion, a curved portion 332 is provided. Adjacent to the first end 331 of the intermediate portion 330, a first concave shaped curvature section 332a is provided. A second convex shaped curvature section 332c is coupled to the first curvature section 332a. Between the first sealing portion 320 and the first concave shaped curvature section 332c, the wall of the intermediate portion is curved outwardly, thus creating the second volume V2. Accordingly, the sealing portion 310 will be pressed against the breast of a user and is therefore in direct contact with the breast of a user. The first concave shaped curvature section 332 will extend away from the breast of a user in a concave shape. The second curvature section 332c will, however, because of its convex shape, extend again towards the breast of a user. In between the second curvature section 332c and the second end 333 of the intermediate portion 330, the intermediate portion is designed to substantially follow a curvature of the areola and the nipple of the breast of a user.

The angle at which the first curvature section 332a extends away from a breast 200 of the user when the intermediate portion is in contact with the breast is smaller than 90°. The presence of the concave shaped first curved section 332a forms part of the intermediate portion 330 which does not come into contact with the nipple of a user when the intermediate portion is pressed against a breast of a user.

Figure 16C:
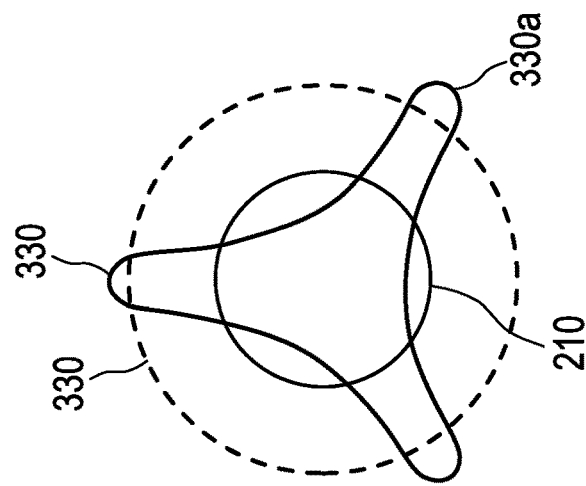
FIGS. 16A to 16C show schematic views of a collapsible intermediate portion according to an aspect of the invention.
Figure 16B:
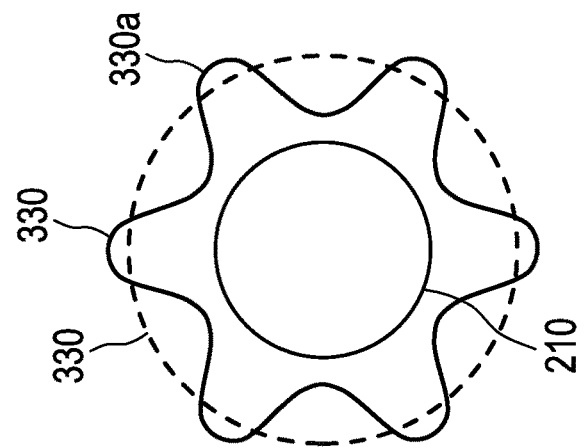
Figure 16A:
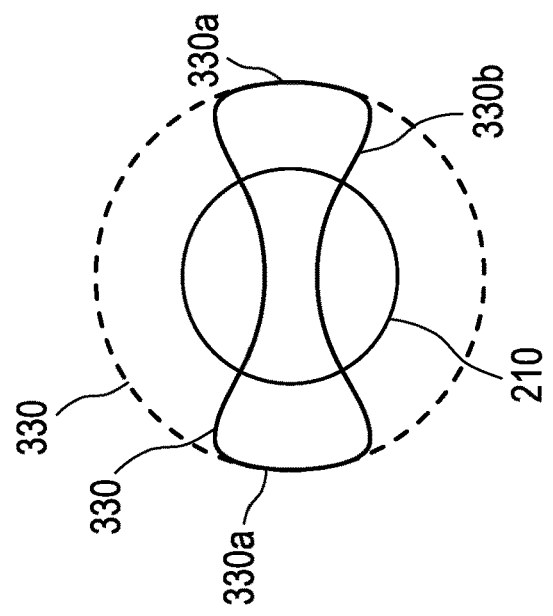

FIGS. 16A to 16C show schematic views of a collapsible intermediate portion according to an aspect of the invention. The FIGS. 16A 16C are used to illustrate a side view of the intermediate portion 330 with its circumferentially extending wall 330b. In FIG. 16A, a front view of an insert for a breast shield arrangement is disclosed. When the collapsible portion has collapsed, the intermediate portion 330 will have two lopes 330a. In the FIGS. 16A 16C, the intermediate portion 330 is shown in an uncollapsed state (broken lines) and in a collapsed state (solid lines). FIG. 16B shows an intermediate portion 330 which comprises, when collapsed, a plurality of lopes 330a. In FIG. 16C, an intermediate portion 330 is depicted which when collapsed comprises three lopes 330a. The intermediate portion 330 according to FIG. 16C constitutes a preferred aspect of the invention. Due to the dimensions of the intermediate portion 330 (in particular due to the reduced length of the intermediate portion 330), the intermediate portion 330 comprises several lopes when the intermediate portion is in a collapsed state. In order to increase the surface of the nipple 210 of the user which is in direct contact with the intermediate portion 330 when it has collapsed, it is advantageous if the number of lopes is reduced (as compared between FIG. 16B and FIG. 16C).

Figure 17D:
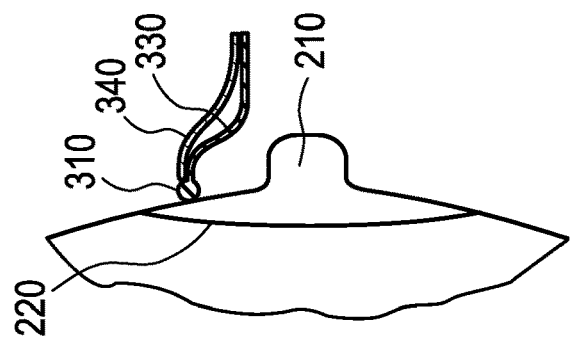
FIGS. 17A to 17D show schematic cross sections of a collapsible intermediate portion according to an aspect of the invention.
Figure 17C:
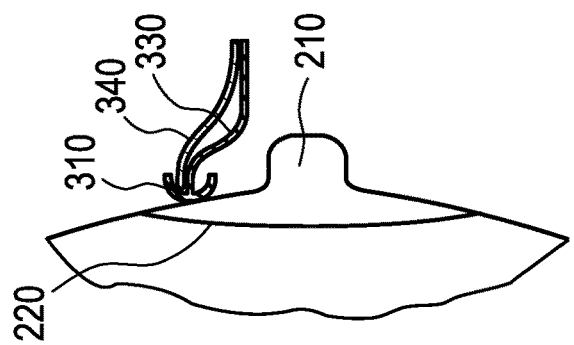
Figure 17B:
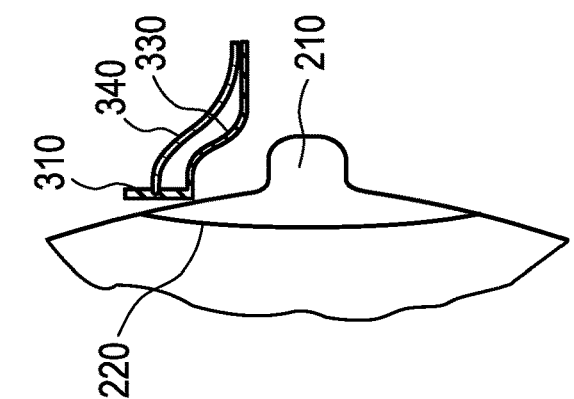
Figure 17A:
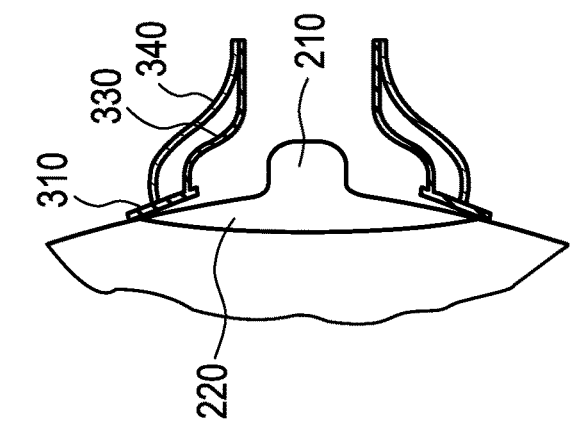

FIGS. 17A to 17D show schematic cross sections of a collapsible intermediate portion according to an aspect of the invention. In the FIGS. 17A 17D, several possible structures of the sealing portion 310 are depicted. In FIG. 17A, the sealing portion 310 has a funnel shape. In FIG. 17B, the sealing portion is only partly in contact with the breast of a user. In FIG. 17C, the sealing portion has a convex or semi-circular shape. In FIG. 17D, the sealing portion may be circular.

Although all these different structures for the sealing unit are possible, the sealing unit of FIG. 17A, namely in form of a funnel, can be a preferred solution.

FIGS. 18A to 18E show schematic cross sections of a breast shield arrangement during the operation of the breast shield arrangement. FIG. 18A shows the situation at the starting of the milk extraction. A breast of a user 200 is placed into a first volume V1 defined by the breast shield arrangement and in particular the intermediate portion 330. In FIG. 18B, a stimulation mode is depicted and a vacuum is applied and the intermediate portion 330 collapses. In particular, the concave portion 332 of the intermediate portion 330 comes into contact with the nipple 210 (and possibly the areola 220). Hence, a second volume V2 is created between the first sealing portion 310 and the curved portion 332. FIG. 18C shows a next step of the vacuum cycle, namely where the vacuum is released and the intermediate portion 330 is released from its collapsed shape. FIG. 18D shows a further step in the vacuum cycle where the concave portion 332a of the intermediate portion 330 is in contact with the nipple 210 of the user creating a second volume V2 and due to the applied to the vacuum, the nipple 210 is stretched towards the second end 320 of the breast shield arrangement 300. In other words, a convex section 332c is in contact with the nipple 210 (and possibly the areola 220) of a user while the concave section 332a is not in contact with the nipple 210 or areola 220 of the user. However, with increased vacuum and depending on the flexibility of the breast/areola tissue, the concave section 332a may be filled with breast tissue. Thus, a second volume V2 is created which is (at least partly) sealed off from the vacuum in the expression kit 501 and in the area of the second end 320 of the breast shield arrangement 300. When the vacuum is further applied as disclosed in FIG. 18E, a part of the collapsible intermediate portion 330 between the concave section 332c and the second end 320 of the intermediate portion 330 comes into contact with the nipple 220. Thus, the volume in front of the nipple and the second end 320 is under a greater vacuum. As a greater surface of the nipple is in contact with the collapsed intermediate portion 330, the nipple will not be stretched as in prior art breast pumps.

The touching of the nipple by the collapsed intermediate portion as shown in FIG. 18E is advantageous as it improves the milk let down. Furthermore, as the volume which is under vacuum is reduced (as compared between the FIGS. 18D and 18E), the vacuum is applied to the tip of the nipple 210.

FIG. 19 shows a schematic cross section of a breast shield arrangement according to an aspect of the invention. In FIG. 19, the first and second sealing portion of the breast shield arrangement is shown in more detail. The first sealing portion 310 is that portion where the breast shield arrangement is pressed against the breast or areola of a user when the breast is placed into the first volume V1 defined by the breast shield arrangement. When a vacuum is applied to the first volume V1 and the second sealing portion 332c comes into contact with the nipple 210 or the areola 220 of a user thus creating a second volume V2 which may not be in contact with the first volume V1.

FIG. 20 shows a schematic cross section of a breast shield arrangement according to an aspect of the invention. In FIG. 20, three different shapes of the intermediate portion 330 are depicted. In the left hand side picture, the intermediate portion 330 comprises a concave section and a convex section. In the middle picture of FIG. 20, the intermediate portion 300 has a step shape and in the right hand figure of FIG. 20, the intermediate portion 330 has a T-shaped cross section towards a second end.

Figure 21:
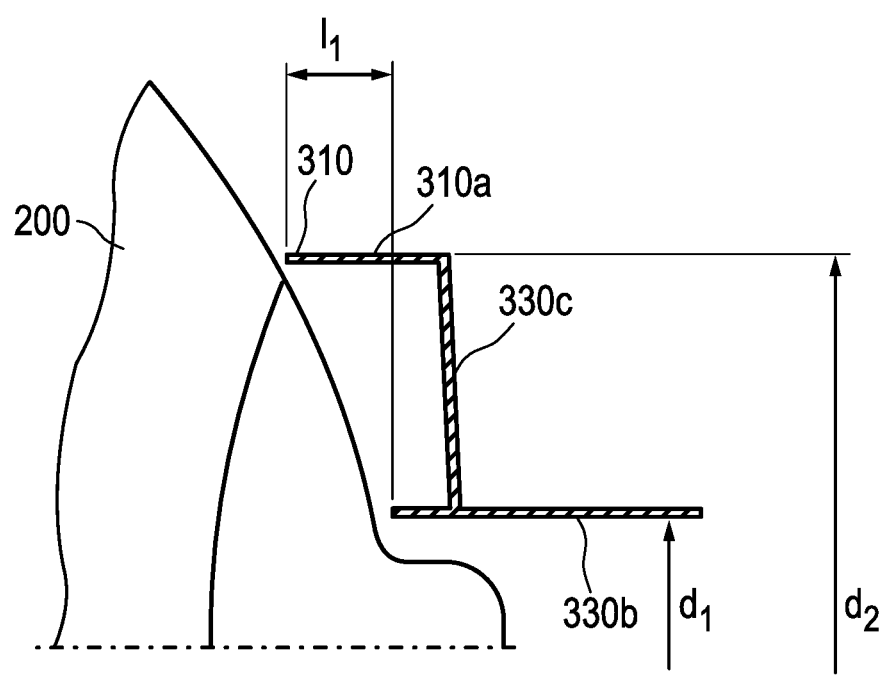
FIG. 21 shows a schematic cross section of a breast shield arrangement according to an aspect of the invention.

FIG. 21 shows a schematic cross section of a breast shield arrangement according to an aspect of the invention. In FIG. 21, the breast shield arrangement can be defined by the diameter d1 and d2 as well as length $l_1$.

According to the invention, the only vacuum that is applied to the breast shield arrangement for expressing milk is applied via the port 320. There is no need for any other vacuum. The milk expression is achieved by the vacuum at the port and the structure of the intermediate portion.

Other variations of the disclosed embodiment can be understood and effected by those skilled in the art in practicing the claimed invention from a study of the drawings, the disclosure and the appended claims.

In the claims, the word "comprising" does not exclude other elements or steps and in the indefinite article "a" or "an" does not exclude a plurality.

A single unit or device may fulfil the functions of several items recited in the claims. The mere fact that certain measures are recited in mutual different dependent claims does not indicate that a combination of these measurements cannot be used to advantage. A computer program may be stored/distributed on a suitable medium such as an optical storage medium or a solid state medium, supplied together with or as a part of other hardware, but may also be distributed in other forms such as via the internet or other wired or wireless telecommunication systems.

Any reference signs in the claims should not be construed as limiting the scope.

The invention claimed is:

1. A breast shield arrangement for a breast pump, the breast shield arrangement comprising:
   a first sealing portion adapted to seal the breast shield arrangement against a breast of a user;
   a port adapted to be coupled to an expression kit or to be a part of the expression kit; and
   an intermediate portion coupled to the first sealing portion and the port,
   said intermediate portion having a circumferentially extending wall defining a first volume adapted to receive a part of the breast including a nipple and at least part of an areola,
   said intermediate portion having a first end, a curved portion and a second end,
   wherein the curved portion comprises a second sealing portion,
   said second sealing portion being adapted to seal at least part of the curved portion against the nipple of the part of the breast received by the intermediate portion when a vacuum is applied at the port of the breast shield arrangement, thereby creating a second volume between the first and second sealing portions and the breast,
   wherein the curved portion at the second volume is curved outwardly as seen from the first sealing portion.

2. The breast shield arrangement according to claim 1, wherein a cross-sectional area of the curved portion is continuously reduced from a first end of the curved portion to a second end of the curved portion.

3. The breast shield arrangement according to claim 1, wherein the curved portion has at least a concave shape at the first end of the intermediate portion and a convex shape near the second end of the intermediate portion.

4. The breast shield arrangement according to claim 1, wherein a ratio between a diameter of the second sealing portion and a total length of the breast shield arrangement is >1.

5. The breast shield arrangement according to claim 1, wherein a ratio between a diameter of the second sealing portion and a length of the curved portion of the breast shield arrangement is >1.

6. The breast shield arrangement according to claim 1, wherein
   when no vacuum is applied to the breast shield arrangement via the port, the intermediate portion is configured such that the nipple of the breast can be inserted without coming in contact with the curved portion.

7. The breast shield arrangement according to claim 1, wherein the intermediate portion is flexible and collapsible and in a collapsed state has a cross section with at least two lobes.

8. The breast shield arrangement according to claim 1, wherein a wall thickness of the curved portion is substantially constant.

9. The breast shield arrangement according to claim 1, wherein the curved portion comprises a first end, a second end, a first curved section, and second curved section,
wherein the first curved section is of a concave shape,
wherein the second curved section is of a convex shape,
wherein the first and second ends of the curved portion correspond to the first and second ends of the intermediate portion, respectively, and
wherein the first and/or second curved section correspond to a first contact point being a first point of contact with the nipple of the breast when the vacuum is applied to the breast shield arrangement and the intermediate portion collapses.

10. The breast shield arrangement according to claim 1, further comprising:
a support structure at least partly surrounding the first sealing portion and the intermediate portion, wherein the support structure is made of a rigid material, and wherein the first sealing portion and the intermediate portion form an insert and are made of a soft and flexible material.

11. An expression kit for a breast pump, comprising a housing and the breast shield arrangement according to claim 10, wherein at least part of the support structure and at least part of the housing are manufactured as one piece.

12. A breast pump, comprising
a vacuum generating unit;
a vacuum conduit coupled to the vacuum pump; and
the breast shield according to claim 1,
wherein the breast shield is coupled to the vacuum generating unit via the vacuum conduit.

13. The breast shield arrangement according to claim 1, wherein the at least part of the curved portion of the intermediate portion comes into contact first with the nipple and thereafter the areola of the breast when the vacuum is applied to the breast shield arrangement to provide the second sealing portion.

14. A breast shield arrangement for a breast pump, the breast shield arrangement comprising:
a sealing portion adapted to seal the breast shield arrangement against a breast of a user;
a port adapted to be coupled to an expression kit or to be a part of the expression kit; and
an intermediate portion coupled to the sealing portion and the port and adapted to receive part of the breast including a nipple and at least part of an areola,
said intermediate portion having a first end, a second end, and a curved portion with a first end and a second end,
wherein a length of the curved portion is greater than a distance between the first end and the second end of the curved portion,
wherein the curved portion has at least a concave shape at the first end of the intermediate portion as seen from the sealing portion,
wherein the curved portion comprises another sealing portion being adapted to seal at least part of the curved portion against the nipple of the part of the breast received by the intermediate portion when a vacuum is applied at the port of the breast shield arrangement, thereby across-sectional area of the curved portion is reduced from the first end to the second end of the curved portion.

15. A method of operating a breast shield arrangement for a breast pump, wherein the breast shield arrangement comprises a first sealing portion, a port and an intermediate portion coupled to first sealing portion and the port, wherein the intermediate portion comprises a circumferentially extending wall defining a first volume, wherein the intermediate portion has a curved portion, the method comprising:
placing the intermediate portion over part of a breast of a user including a nipple and at least part of an areola;
sealing the breast shield arrangement against the breast by the first sealing portion;
coupling the port of the breast shield arrangement to an expression kit;
applying a vacuum to the port of the breast shield arrangement by a vacuum generating unit such that a second sealing portion of the curved portion is brought into contact against the nipple and at least part of the areola of the breast, wherein the vacuum applied to the port is the only vacuum in the breast shield arrangement; and
creating a second volume between the first and second sealing portions and the breast when the second sealing portion comes into contact against the nipple and the at least part of the areola of the breast,
wherein the curved portion at the second volume is curved outwardly away from the breast.

16. A non-transitory computer readable medium storing that, when executed by a processor, cause the processor to carry out the steps of the method of claim 15.

17. The method according to claim 15, wherein applying the vacuum to the port of the breast shield arrangement causes the second sealing portion of the curved portion to be brought into contact first with the nipple of the areola of the breast.

18. The method according to claim 15, further comprising:
when no vacuum is applied to the breast shield arrangement via the port, inserting the nipple of the breast in the intermediate portion without coming in contact with the curved portion.

19. The method according to claim 15, wherein the intermediate portion is flexible and collapsible and in a collapsed state has a cross section with at least two lobes.

20. The method according to claim 15, wherein a wall thickness of the curved portion is substantially constant.

* * * * *